United States Patent
Kermani et al.

(10) Patent No.: US 10,068,053 B2
(45) Date of Patent: Sep. 4, 2018

(54) BASECALLER FOR DNA SEQUENCING USING MACHINE LEARNING

(71) Applicant: Complete Genomics, Inc., Mountain View, CA (US)

(72) Inventors: Bahram Ghaffarzadeh Kermani, Los Altos, CA (US); Radoje Drmanac, Los Altos Hills, CA (US)

(73) Assignee: Complete Genomics, Inc., San Jose, CA (US)

( * ) Notice: Subject to any disclaimer, the term of this patent is extended or adjusted under 35 U.S.C. 154(b) by 803 days.

(21) Appl. No.: 14/571,022

(22) Filed: Dec. 15, 2014

(65) Prior Publication Data
US 2015/0169824 A1    Jun. 18, 2015

Related U.S. Application Data

(60) Provisional application No. 61/916,682, filed on Dec. 16, 2013.

(51) Int. Cl.
| | |
|---|---|
| *G01N 33/48* | (2006.01) |
| *G01N 33/50* | (2006.01) |
| *G06F 19/24* | (2011.01) |
| *G06F 19/22* | (2011.01) |

(52) U.S. Cl.
CPC .............. *G06F 19/24* (2013.01); *G06F 19/22* (2013.01)

(58) Field of Classification Search
None
See application file for complete search history.

(56) References Cited

U.S. PATENT DOCUMENTS

| | | |
|---|---|---|
| 5,502,773 A | 3/1996 | Tibbetts et al. |
| 5,972,602 A | 10/1999 | Hyland et al. |
| 6,260,034 B1 | 7/2001 | Björkesten |
| 8,518,640 B2 | 8/2013 | Drmanac |
| 2003/0225526 A1 | 12/2003 | Golub et al. |
| 2011/0256631 A1 | 10/2011 | Tomaney et al. |
| 2012/0046177 A1 | 2/2012 | Huang et al. |
| 2013/0059740 A1 | 3/2013 | Drmanac et al. |
| 2013/0157264 A1 | 6/2013 | Obara et al. |
| 2013/0236895 A1 | 9/2013 | Faham et al. |

(Continued)

OTHER PUBLICATIONS

Drmanac, Radoje, et al., "Human genome sequencing using unchained base reads on self-assembling DNA nanoarrays," Science, 2010, vol. 327, pp. 78-81.

(Continued)

*Primary Examiner* — Russell Scott Negin
(74) *Attorney, Agent, or Firm* — Kilpatrick Townsend & Stockton LLP

(57) ABSTRACT

Methods, systems, and apparatuses are provided for creating and using a machine-leaning model to call a base at a position of a nucleic acid based on intensity values measured during a production sequencing run. The model can be trained using training data from training sequencing runs performed earlier. The model is trained using intensity values and assumed sequences that are determined as the correct output. The training data can be filtered to improve accuracy. The training data can be selected in a specific manner to be representative of the type of organism to be sequenced. The model can be trained to use intensity signals from multiple cycles and from neighboring nucleic acids to improve accuracy in the base calls.

19 Claims, 12 Drawing Sheets

(56) References Cited

U.S. PATENT DOCUMENTS

2014/0051588 A9     2/2014     Drmanac

OTHER PUBLICATIONS

Peters, Brock, et al., "Accurate whole-genome sequencing and haplotyping from 10 to 20 human cells," Nature, 2012, vol. 487, pp. 190-195.

Kao, Wei-Chun, et al., "BayesCall: A model-based base-calling algorithm for high-throughput short-read sequencing," Genome Research, 2009, vol. 19, pp. 1884-1895.

Kao, Wei-Chun, "Algorithms for next-generation high-throughput sequencing technologies," Technical Report No. UCB/EECS-2011-99, Sep. 2, 2011, Electrical Engineering and Computer Sciences University of California at Berkeley, 108 pages.

Golan, David, et al., "Using state machines to model the ion Torrent sequencing process and to improve read error rates," Bioinformatics, 2013, vol. 29, pp. i344-i351.

Kircher, Martin, et al., "Improved base calling for the Illumina Genome Analyzer using machine learning strategies," Genome Biology, 2009, vol. 10, 9 pages.

Erlich, Yaniv, et al., "Alta-Cyclic: a self-optimizing base caller for next-generation sequencing," Nat Methods, 2008, vol. 5, No. 8, pp. 679-682.

Ledergerber, Christian, et al., "Base-calling for next-generation sequencing platforms," Briefings in Bioinformatics, Jan. 18, 2011, 9 pages.

PCT/US2014/070375, "International Search Report and Written Opinion", dated Mar. 18, 2015, 21 pages.

Extended European Search Report received in European Patent Application No. 14871415.7, dated Jul. 24, 2017. 9 pages.

Massingham, T. et al. *All Your Base: A Fast and Accurate Probabilistic Approach to Base Calling.* Genome Biology, vol. 13, No. 2. Published Feb. 29, 2012. 15 pages.

|  Observed<br>Expected | A | C | G | T |
|---|---|---|---|---|
| A | 30 |  |  |  |
| C |  | 20 |  |  |
| G |  |  | 20 |  |
| T |  |  |  | 30 |

FIG. 9A

| Observed<br>Expected | A | C | G | T |
|---|---|---|---|---|
| A | 30.83 | 0.115 | 0.139 | 0.153 |
| C | 0.133 | 19.30 | 0.085 | 0.097 |
| G | 0.18 | 0.088 | 20.72 | 0.092 |
| T | 0.177 | 0.105 | 0.092 | 27.70 |

FIG. 9B

BASECALLER FOR DNA SEQUENCING USING MACHINE LEARNING

CROSS-REFERENCES TO RELATED APPLICATIONS

This application claims the benefit of U.S. Provisional Application No. 61/916,682 entitled "Basecaller For DNA Sequencing Using Machine Learning," filed Dec. 16, 2013, the entirety of which is incorporated by reference herein.

BACKGROUND

In genetics, the term sequencing may refer to methods for determining a primary structure or sequence of a biopolymer, including a nucleic acid (e.g., DNA, RNA etc.). More specifically, DNA sequencing is the process of determining an order of nucleotide bases (adenine, guanine, cytosine and thymine) in a given DNA fragment. Such sequencing methods commonly include calling a base at a position in a nucleic acid, where the called base is used to determine a sequence for the nucleic acid.

When sequencing target nucleic acids, for example, the process typically includes extracting and fragmenting target nucleic acids from a sample. The fragmented nucleic acids are used to produce target nucleic acid templates that will generally include one or more adapters. The target nucleic acid templates may be subjected to amplification methods, such as bridge amplification to provide a cluster or rolling circle replication to provide a nucleic acid "nanoball." Sequencing applications are then performed on the single-stranded nucleic acids, e.g., by sequencing by synthesis or by ligation techniques, including combinatorial probe anchor ligation (cPAL).

An intensity value (e.g., a fluorescence signal) corresponding to a base that is incorporated into a nucleic acid at a particular position can indicate the base at that position. For example, four different types of fluorescence may be used, corresponding to the four types of bases to be identified. The nucleic acids are amenable to relatively inexpensive and efficient imaging techniques in which the nucleic acids are captured in four color images, one for each type of fluorescence used. The four images can then be processed through software to extract intensity information. Examples of incorporation are synthesis, ligation, and hybridization.

As mentioned above, the intensity values (signals) can be used to call a base at a position of the nucleic acid, i.e., perform basecalling. The intensity value for a target nucleic acid template can correspond to one pixel or multiple pixels of an image, or there can be multiple templates for a pixel (i.e., more than one template per pixel). Regardless, an intensity value for each of the four bases can be assigned to a template. Naively, one can call the base corresponding to the maximum intensity value, but this has a high error rate. For example, the determination of the intensity value can be incorrect due to optical effects (e.g., overlap in spectrum of the various intensity signals) and spatial effects (e.g., when multiple templates correspond to a single pixel). Additionally, the biochemistry of the sequencing process can cause artifacts and the intensity signals can vary significantly from one position and template to another (e.g., due to differences in amplification of one template to another), and from sample to sample.

Accordingly, it would be desirable to provide improved methods and systems for making base calls.

BRIEF SUMMARY

Embodiments provide methods, apparatuses, and systems for creating and using a basecalling model. As an example, the basecalling model can be created using training data (e.g., inputs of intensity values and outputs of sequences assumed to be correct) from one or more earlier sequencing runs, and then the basecalling model can be used in a later sequencing run, e.g., weeks or months after the earlier sequencing run(s). The training data can be assembled over an extended period of time to obtain high accuracy in the training data (e.g., by using stringent settings that would not normally be used in a production run) and to provide a training data set that is representative of samples to be sequenced in a production run. A substantial amount of training data can be obtained, with an optimization process for determining the model occurring over an extended period of time (e.g., days or weeks).

According to one embodiment, to obtain accurate training data, initial base calls can be made (e.g., using an initial basecaller). The initial base calls can be used to create initial sequences of nucleic acids. These initial sequences can be filtered, e.g., to remove inaccurate data, sequences that are likely to be inaccurate, base calls that are or are likely to be inaccurate, and/or apply weights to base calls or entire sequences to reduce a respective contribution to a cost function for optimizing the basecalling model. Such filtering can be performed in embodiments where the basecalling model is trained on data obtained during a production run.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 9A shows an ideal confusion matrix. FIG. 9B shows a confusion matrix according to embodiments of the present invention.

DEFINITIONS

Figure 1:
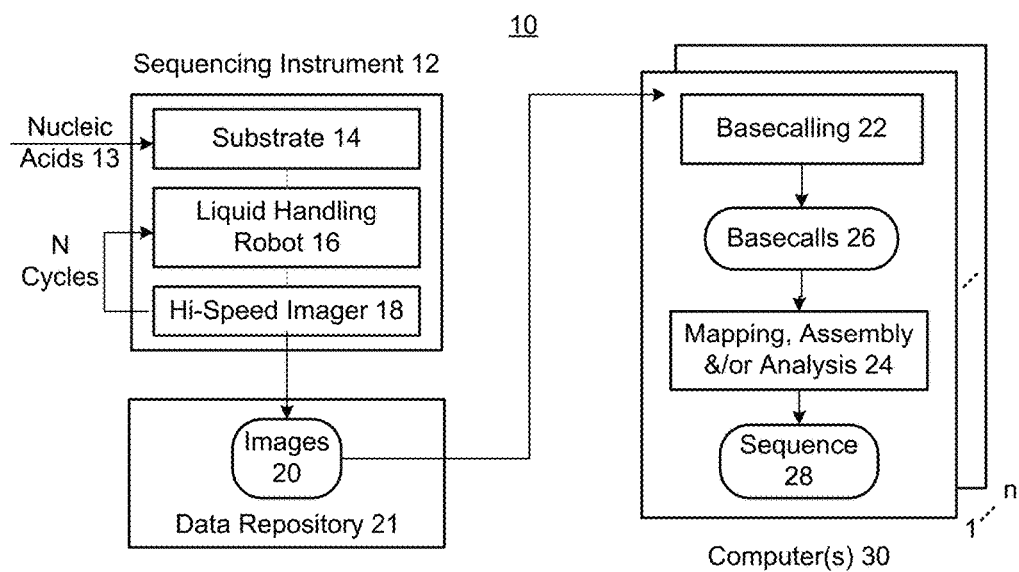
FIG. 1 is a block diagram illustrating an example system 10 for basecalling using intensity values (e.g., as determined from digital images) of nucleic acids according to one embodiment.

The following definitions may be helpful in providing background for an understanding of embodiments of the invention.

A "sequence read" or "read" refers to data representing a sequence of monomer units (e.g., bases) that comprise a nucleic acid molecule (e.g., DNA, cDNA, RNAs including mRNAs, rRNAs, siRNAs, miRNAs and the like). The sequence read can be measured from a given molecule via a variety of techniques.

As used herein, a "fragment" refers to a nucleic acid molecule that is in a biological sample. Fragments can be referred to as long or short, e.g., fragments longer than 10 Kb (e.g. between 50 Kb and 100 Kb) can be referred to as long, and fragments shorter than 1,000 bases can be referred to as short. A long fragment can be broken up into short fragments, upon which sequencing is performed.

A "mate pair" or "mated reads" or "paired-end" can refer to any two reads from a same molecule (also referred to as two arms of a same read—arm reads) that are not fully overlapped (i.e., cover different parts of the molecule). Each of the two reads would be from different parts of the same molecule, e.g., from the two ends of the molecule. As another example, one read could be for one end of the molecule in the other read for a middle part of the molecule. As a genetic sequence can be ordered from beginning to end, a first read of a molecule can be identified as existing earlier in a genome than the second read of the molecule when the first read starts and/or ends before the start and/or end of the second read. More than two reads can be obtained for each molecule, where each read would be for a different part of the molecule. Usually there is a gap (mate gap) from about 100-10,000 bases of unread sequence between two reads. Examples of mate gaps include 500+/−200 bases and 1000+/−300 bases.

"Mapping" or "aligning" refers to a process which relates a read (or a pair of reads, e.g., of a mate pair) to zero, one, or more locations in a reference sequence to which the read is similar, e.g., by matching the instantiated arm read to one or more keys within an index corresponding to a location within a reference As used herein, an "allele" corresponds to one or more nucleotides (which may occur as a substitution or an insertion) or a deletion of one or more nucleotides. A "locus" corresponds to a location in a genome. For example, a locus can be a single base or a sequential series of bases. The term "genomic position" can refer to a particular nucleotide position in a genome or a contiguous block of nucleotide positions. A "heterozygous locus" (also called a "het") is a location in a reference genome or a specific genome of the organism being mapped, where the copies of a chromosome do not have a same allele (e.g. a single nucleotide or a collection of nucleotides). A "het" can be a single-nucleotide polymorphism (SNP) when the locus is one nucleotide that has different alleles. A "het" can also be a location where there is an insertion or a deletion (collectively referred to as an "indel") of one or more nucleotides or one or more tandem repeats. A single nucleotide variation (SNV) corresponds to a genomic position having a nucleotide that differs from a reference genome for a particular person. An SNV can be homozygous for a person if there is only one nucleotide at the position, and heterozygous if there are two alleles at the position. A heterozygous SNV is a het. SNP and SNV are used interchangeably herein.

Sequencing refers to the determination of intensity values corresponding to positions of one or more nucleic acids. The "intensity values" can be any signal, e.g., electrical or electromagnetic radiation, such as visible light. There can be one intensity value per base, multiple intensity values per base, or fewer intensity values than there are bases. Also, an intensity value can be for a particular position, or an intensity value can be for multiple positions of a nucleic acid. Intensity values can be restricted to predetermined values (e.g., binary or integers in a decimal numeral system), or can have continuous values.

A "sequencing process" or "sequencing run" refers to the determination of intensity values corresponding to positions of one or more nucleic acids as a batch. For example, when the sequencing involves imaging biochemical reactions of nucleic acids on a substrate, the resulting intensity values are obtained during the same sequencing run. Intensity values of nucleic acids for a different substrate would appear in different sequencing runs. A nucleic acid of a first sequencing run would not be involved in a second sequencing run (e.g., not included in a same image).

An "assumed sequence" corresponds to the sequence that is believed to be accurate. The determination may be inaccurate, but the training assumes it is accurate. The assumed sequence can be determined in a variety of ways, e.g., as described herein. An assumed sequence can include no calls, and thus an assumed sequence can have open positions between called positions.

A "machine-learning model" (also referred to as a model) refers to techniques that predict output base calls based on known results (training data). The known results can be an assumed sequence, which is assumed to be correct. As the model attempts to predict the results of the training data, the machine learning can be supervised learning, where the supervision comes from the training data.

A "base call" is a determination of a base at a position in a nucleic acid. A base call can be a no-call or a specified base. A base call can be made independently or as part of a combination of specified base (e.g., A/T), which can be for a same genomic position (e.g., if respective scores are close to each other) or for multiple positions. A "score" output from a machine-learning model can be used to determine a base call at a position. For example, a score can be provided for each of the bases. The determination of the base call based on the scores can be considered part of the model. Some models can provide a score, where the scores are used by a later process. Examples of a score can be a probability or a possibility. The probability scores for each of the bases would sum to a fixed number, i.e., one. The possibility scores are not required to sum to the fixed number. Each possibility score can be constrained to be between 0 and 1. The possibility scores could sum to 1, particularly if a model is trained well.

DETAILED DESCRIPTION

Embodiments can provide a machine-learning model for determining base calls from intensity values output from a sequencing process. The model can be created in various forms, e.g., as single-cycle or multi-cycle, using only the nucleic acid molecule of interest or also using the neighboring nucleic acid molecules, restricted to a particular region of the genome or applicable to the entire genome, etc.

Embodiments can be applied to any sequencing technique that outputs intensity values for two or more bases. The intensity values for a given sequencing cycle can be obtained simultaneously (e.g., multi-cycle) or sequentially (e.g., when each base is added and removed from the sample before adding a next base). Embodiments can be applied to sequencing techniques that amplify a nucleic acid template or single molecule techniques that do not amplify. Various amplification techniques can also be used. Sequencing by synthesis (SBS) or sequencing using ligation, as well as other techniques, may be used to provide the intensity values. Herein, any discussion referring to a DNB (DNA nano-ball) as a nucleic acid molecule of interest is equally relevant to other techniques. Thus, embodiments can be applied to various sequencing techniques.

I. Basecalling

Various sequencing techniques can be used to obtain intensity values. For example, many nucleic acid molecules can be deposited on a substrate (slide). The molecules can be deposited in an ordered array (lattice), e.g., a rectangular (including square), checkerboard (lattice positions neighboring corners and not sides, such as black boxes on a checkerboard), or hexagonal lattice, or in a non-ordered fashion. Distinct locations on the substrate can correspond to different starting molecules. In other embodiments, the molecules can flow through channels within which sequencing is performed.

During the sequencing process, intensity values from molecules on a given substrate can be obtained simultaneously for a given cycle, where each cycle corresponds to a different position on a molecule. For example, an image of a substrate can include different locations that emit light, where each position can emit signals of different wavelengths for each base. An image can correspond to a particular cycle. As mentioned above, the intensity values obtained from sequencing can be used to call a base at a position of each of the nucleic acid molecules.

FIG. 1 is a block diagram illustrating an example system 10 for basecalling using intensity values (e.g., as determined from digital images) of nucleic acids according to one embodiment. In this embodiment, system 10 may include a sequencing instrument 12 and a cluster of one or more computers 30. The computers 30 may be connected to the sequencing instrument 12 via a direct wired or wireless connection or via a high-speed local area network (not shown). The sequencing instrument 12 may include primary sub-systems, such as a substrate 14 for holding nucleic acids 13, a liquid handling robot 16, and a high-speed imager 18. At least a portion of the computers 30 may execute instances of software components in parallel, including a basecalling component 22 (which may utilize a machine-learning model) and a Mapping, Assembly &/or Analysis component 24.

Computers 30 may include typical hardware components (not shown) including, one or more processors, input devices (e.g., keyboard, pointing device, etc.), and output devices (e.g., a display device and the like). Computers 30 may include computer-readable/writable media, e.g., memory and storage devices (e.g., flash memory, a hard drive, an optical disk drive, a magnetic disk drive, and the like) containing computer instructions that implement the functionality disclosed when executed by the processors. Computers 30 may further include software and/or hardware for controlling the sequencing instrument 12 and computer writeable media for storing the base calls 26.

Sequencing can operate on input nucleic acids 13, which may be obtained by extracting larger molecules from a sample or target organism and fragmenting them. In various embodiments, nucleic acids 13 may be derived from a gene, a regulatory element, genomic DNA, cDNA, RNAs including mRNAs, rRNAs, siRNAs, miRNAs and the like and fragments thereof. Any suitable sequencing technique may be used to provide intensity values, e e.g., as described in U.S. Pat. No. 8,518,640; US Patent Publication 2014/0051588 entitled "Sequencing Small Amounts of Complex Nucleic Acids" by Drmanac et al., filed Apr. 16, 2012, the disclosures of which are incorporated by reference in its entirety; Drmanac et al., Science 327:78-81, 2010; and Peters et al., Nature 487:190-195, 2012. In one embodiment, nucleic acids 13 are placed onto one or more substrates 14, and the substrates 14 are then inserted into the sequencing instrument 12. Substrate 14 may be either un-patterned or patterned. In the un-patterned embodiment, samples of nucleic acid may each be deposited in discrete locations on the substrate 14, but the locations need not be fixed.

In one embodiment where fluorescence detection is used, high-speed imager 18 may form a four-color fluorescence microscope. In one implementation, each position on one of the nucleic acids can be imaged for each cycle. Substrate 14 can be divided up into fields, which may form lanes. Images can be taken of one field at a time, with all fields being imaged once for a cycle. High-speed imager 18 may store images 20 in a data repository 21.

Images 20 from data repository 21 can be processed by basecalling component 22 for generation of base calls 26. Basecalling component 22 comprises program instructions that process the images 20 to identify the bases (e.g., nucleotides A, T, G or C) at each position in the nucleic acid 13. Different positions can correspond to different sequential sequencing/reaction cycles (hereinafter, "cycles"). During each cycle, a different position of a nucleic acid 13 is interrogated and at least one image of the nucleic acid 13 is captured. The basecalls 26 for each position in a nucleic acid 13 may be collated to form a sequence read. As described below, basecalling component 22 can include multiple stages of basecalling, as well as mapping and assembly, particularly when system 10 is used in a training mode.

After final base calling is performed, Mapping, Assembly &/or Analysis component 24 may operate on the sequence reads and may produce a variety of outputs, including reads aligned to a reference genome (not shown) and consensus sequence assembly of overlapping reads, shown as sequence 28. Sequence 28 can be output and analyzed by software or a person to identify characteristics of the organism, e.g., whether the organism has a particular disease, is predisposed to a particular disease, has a particular genetic trait, etc.

A. Single Cycle

In a single-cycle basecaller, the intensity values for the current position (cycle) of the nucleic acid are used to call the base at the current position, and the intensity values for other cycles are not used. A cycle can be performed in various ways. In one embodiment, a plurality of probes are added to the system at the same time, and ideally the probes cause a signal only when hybridized to the nucleic acid. The probes would elicit different signals, e.g., different parts of the electromagnetic spectrum. Different electrical signals are also possible. In another embodiment, each probe is added at a time. For example, a probe for only A is added, and a signal (e.g., an electrical or light signal) is obtained corresponding to whether or not A hybridized at the position. Then, the probes can be removed, and a next base can be added, and so on. In this manner, the signals from probes for different bases do not have to be different, since the different signals are differentiated in time.

Typically, the simplest basecalling procedure is to call the base with the highest intensity, e.g., with the added criteria of the highest intensity being above a threshold, with a no call being made if all the intensities are below the threshold. If the intensities are normalized by a weighted sum of the intensities (e.g., normalized intensities to one) the normalized intensities may be considered probabilities. A background signal can be subtracted out before this normalization. An additional factor accounting for variation in intensity signals (e.g., modeling as noise with a Gaussian function) can be used.

However, simply picking a maximum intensity is not very accurate. For example, when the four intensity values are obtained at the same time, there can be crosstalk between the signals emitted by the fluors that are attached to the respective bases. The wavelengths corresponding to the signal of a particular base can be referred to as a channel. A crosstalk matrix can be used to reduce the crosstalk and obtain more accurate intensity values. For example, the intensity of a given channel (e.g., signal for G) for a first position of a first nucleic acid can be calculated as a weighted sum of the intensities of the four channels for the first position of the first nucleic acid. But, such a correction does not account for some optical problems, and does not address variations in the biochemical process.

An additional optical problem arises from bleed of signals from neighboring nucleic acids that affect the measured signals for the nucleic acid whose bases are being called. This bleed from neighboring signals can be addressed using linear or non-linear regression. For example, the intensity of a given channel (e.g., signal for G) for a first position of a first nucleic acid can be calculated as a weighted sum of the intensities of the given channels for the same cycle of the nucleic acids that are neighbors to the first nucleic acid. A fraction of the intensities from the neighbors can be subtracted from the signal for the first nucleic acid. The coefficients for the weighted sum can be determined using measurements of the optical properties of the system. Even when taking into account such factors, such a regression using optical measurements still has limitations in accuracy, e.g., as variations in biochemistry from an experiment to another are not taken into consideration.

B. Multi-Cycle

In a multi-cycle basecaller, intensity values for more than one cycle are used in calling a base at a particular position. For example, the intensity value of a previous cycle can be used in determining the base for the current cycle. The use of an intensity value from a previous cycle can count for variations in biochemistry. For instance, probes from one cycle may not be completely removed before the start of the next cycle; therefore, these remaining probes may still emit a signal corresponding to the base of the previous position. As another example, an improper extension (e.g., more than one) of an adaptor sequence can occur prior to a reading step. Then, as a current position is interrogated, the signal from other positions can contribute.

In various embodiments, any number of previous cycles can be used. Additionally, intensity values for multiple cycles can simultaneously be used to determine bases at corresponding positions. For example, the intensity values for five cycles can be used to determine the bases at the five positions corresponding to those cycles.

As an example, three to five previous cycles can provide enough information about how a particular enzyme is affecting the intensities for a particular experiment. In the extreme case, all the previous cycles can be used, but this results in more data that needs to be stored in addition to the additional computation. In another example, subsequent cycles can also be used. For instance, a base added at cycle X can remain, and thus provide a contribution to the signal at a later cycle. This contribution can help to detect the base at the position for cycle X. Subsequent cycles can also impact a current cycle when ligation is the type of incorporation, since a later base can be in the ligated molecule being using to probe the current base position.

Even if an average contribution to the current intensity can be attributed to the intensity for a previous cycle, the amount and type of variations can be very complex. Therefore, embodiments can use actual data from sequencing runs to determine a model for the basecaller that can handle the complexity. For example, a model can be trained using measured intensities of actual nucleic acids for which a particular sequence is assumed (e.g., bases are known, determined from an initial base call, or determined using a previous iteration of the model). With enough data, the variations in the measured intensities can be accurately mapped to the correct base call using training nucleic acids having an assumed sequence. In one embodiment, the model can be improved by learning from mistakes, e.g., by iteratively improving the model on new training data.

C. Intensity Values

An intensity value can be raw data or a value derived from the raw data. An example is an electrical signal that corresponds to a particular base at a particular time (e.g., the signal is known to correspond to A during a time that probes for A are introduced into the system). The signal for a given base can provide a plurality of raw values, e.g., an intensity at a series of times while a particular probe is attached to the target nucleic acid. These raw values for a given base can all be input into a basecalling model, or only a portion of the values can be input (e.g., a maximum, average, median, or other statistical value). As another example, the raw values can be processed to provide parameterized values. For instance, the raw values can be fit to a function (e.g., a polynomial) and the parameters of the fitted function can be used as intensity values.

Further, there can be less than one intensity value per base. For example, the presence and absence of a particular color signal can indicate two different bases respectively. Thus, two different colors (1 and 2) can be used to call 4 bases. For instance, G can correspond to no signal, A can correspond to a signal of only color 1, T can correspond to a signal of only color 2, and C can correspond to a signal with color 1 and color 2. The intensity values for the two colors can be input to a model to call a base. And, an intensity value can be no signal or a combination of signals, e.g., by converting the intensity values of the two colors to four signals representing the four possibilities.

An intensity value can correspond to more than one base position. For example, a cycle could involve detecting bases at two positions. Each two-base combination could be assigned a different intensity value. Each intensity value for the two-base combinations could correspond to a different color in the spectrum.

II. Machine Learning

As mentioned above, the sequence of a nucleic acid can be used to develop a model that uses measured intensities for determining the sequence of a nucleic acid. The model can be developed using measured intensities for nucleic acids for which the sequence is known. In this manner, a functional relationship between the measured intensities and the correct base call can be determined. Various machine learning methods can be used, such as neural networks and support vector machines. Herein, neural networks are predominately used as an example. Neural networks can enable fast calling (e.g., via feedforward algorithm), can provide outputs that approach probabilities, can allow training algorithms that work with a large volume of training data, and can allow for GPU implementation of the basecaller due to use of simple functions.

Figure 2:
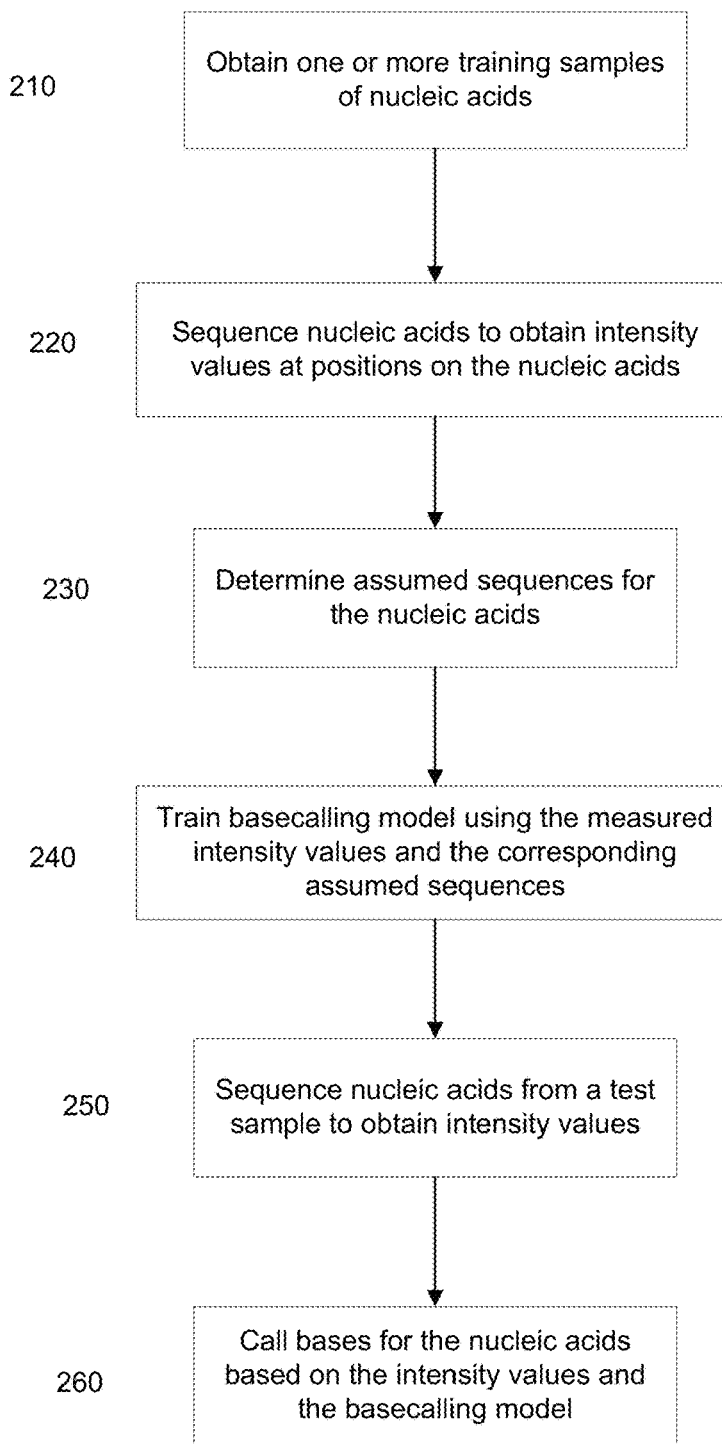
FIG. 2 is a flowchart of a method 200 for developing and using a basecalling model according to embodiments of the present invention.

FIG. 2 is a flowchart of a method 200 for developing and using a basecalling model according to embodiments of the present invention. Various blocks of method 200 (and other methods) may be performed at different times, with later blocks potentially being performed before earlier blocks. All or some of the blocks of method 200 may be performed by the computer system.

At block 210, one or more training samples are obtained. The training samples include nucleic acids that are to be sequenced. The training samples can be nucleic acids from an organism or artificially created nucleic acids, or a mixture of both. The training samples may be from one organism, multiple organisms of the same type (e.g., all human), or from different types of organisms (e.g., from bacteria and human). The training samples may be chosen such that the data is representative of the samples that are to be ultimately analyzed, or to provide a stress case for the samples to be analyzed.

At block 220, a plurality of nucleic acids from the training sample(s) are sequenced to provide intensity values for candidate bases at a plurality of positions on each of the nucleic acids. Any suitable sequencing technique can be used. In some implementations, only a portion of the nucleic acids in any given sample are sequenced.

At block 230, assumed sequences are determined for the sequenced nucleic acids. The assumed sequences can be determined in various ways. The assumed sequence for a nucleic acid can be the actual sequence of the nucleic acid, but also may contain some errors relative to the actual sequence. Techniques can be used to determine the sequence with a high degree of accuracy. The determination of the sequence may use an initial basecaller, along with other techniques (e.g., mapping and assembly), to determine the assumed sequence. One could also use the initial base calls as the assumed sequence. In such a situation, the accuracy may not be improved, but the model can provide greater speed than the initial basecaller.

At block 240, the basecalling model is trained using the measured intensity values for the corresponding assumed sequences. As the output (assumed sequences) is known, parameters of the basecalling model can be chosen to provide the correct output for the assumed sequences, as part of training the model. The output can be a score for each base, where the score can be used to call the base at a given position. As another example, the output can be a single base call for a position, potentially with a confidence score associated with the single base call, as is described in more detail below. All or a portion of the assumed sequences from a given sample may be used. Assumed sequences from various samples can be used to obtain training across various sequencing conditions.

At block 250, a test sample is obtained. The test sample would generally be from an organism whose genome is to be determined by sequencing. Nucleic acids from the test sample can then be sequenced to obtain intensity values, as described herein.

At block 260, the basecalling model uses the intensity values to call bases for the nucleic acids, thereby determining sequences of the nucleic acids. As an example, the basecalling model can include a neural network that receives intensity values and outputs a score for each of the bases, where the score can be used to make the base call. The scores can be used directly (e.g., by taking a maximum of the raw scores) or by processing the scores, e.g., via normalization, weighting, or a softmax activation function. The processed scores can then be analyzed to make the base call.

Accordingly, patterns of behavior and dependencies for different sequences (e.g. CGCG vs. TATA) can be learned by the model. As other examples, spots of different quality DNA and their neighbors in the given experiment (which may have any number of specific characteristics distinct from other experiments) or subset of the experiment, such as part of an array, can also be learned by the model. The training (learning) of the model can provide benefits over the coding of human-extracted heuristics.

III. Training Model

As described above, intensity values and assumed sequences for nucleic acids of one or more training samples are used to train a machine-learning model. Generally, the training is done for a small but representative set of inputs (intensity values) and outputs (assumed sequences). Other inputs could be experimental parameters about the instrument, like average light strength of a laser. In some embodiments, the training can be done over a period of time (e.g., a couple days or weeks) using data from various sequencing runs of training samples. At a later time and for a different sequencing run, the model can be used on a new sample. In other embodiments, the training can be done using data from the same sequencing run for which base calls a desired. This training can use a particular subset of the sequencing data, e.g., a particular lane.

In embodiments where the model is trained at an earlier time, the training is not constrained by the need to obtain sequencing results in a timely fashion. Instead, more effort can be expended to obtain an accurate model. Once the model has been prepared, the use of the model can be quick. For example, a basecalling neural network can be trained over a relatively long period of time and using many computer resources, but the neural network can operate quickly on a regular computer (e.g., a PC) for a production run to obtain the base calls.

Settings for the machine-learning model can be decided before training. For example, it can be determined whether the model is to be single-cycle or multi-cycle, as this will impact how the training is performed. For multi-cycle, it can be determined which cycles are to be included, e.g., the five previous cycles (or other number of previous and/or subsequent cycles) or specific cycles, if not sequential. Other inputs to the model can include intensity values from neighboring nucleic acids on a substrate. Settings can include any values that determine the inputs to the model. Training settings can be fixed values or be selected, such as criteria for determining the assumed sequences.

During an optimization process using a computer system, the model can be trained to automatically learn the intricacies of the underlying data. This training can speed up introduction of experimental and reagent improvements in production, e.g., errors in an assay can be identified more easily, since errors in the basecalling can generally be ruled out. Given that the model provides a flexible framework, the adaptability of the model can relieve the assay development process from "fine-grained" optimization on various variables, including but not limited to the enzyme concentration, dye concentration, dye balance, etc. For example, the model can learn to handle variations in such experimental parameters, thereby obviating very rigid guidelines for these parameters (e.g., by having these experimental parameters as inputs to the model).

A. System

Figure 3:
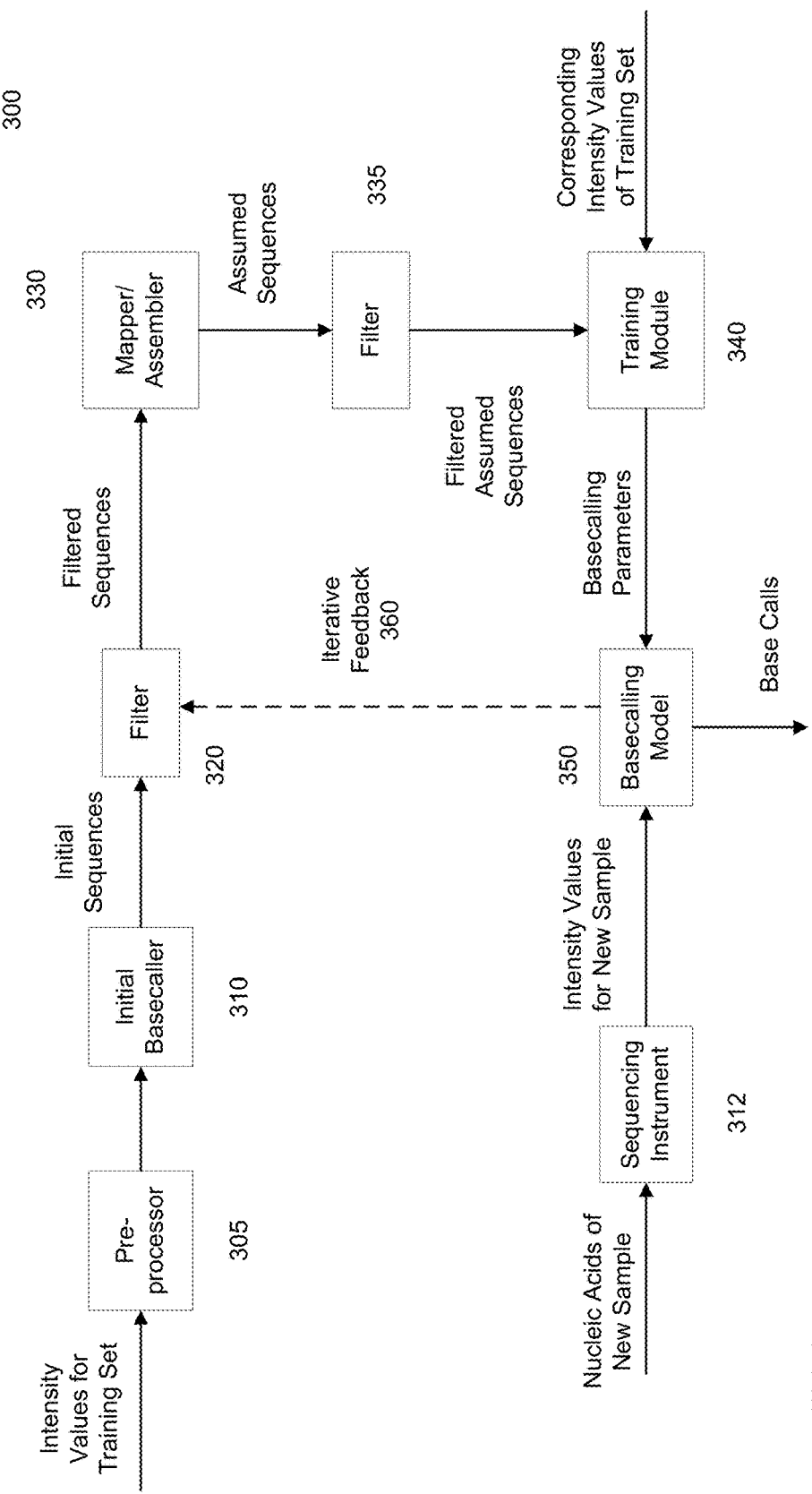
FIG. 3 shows a block diagram of a system 300 for training and using a basecalling model according to embodiments of the present invention.

FIG. 3 shows a block diagram of a system 300 for training and using a basecalling model according to embodiments of the present invention. Components 310-340 can be used to train the model and may be implemented using a first computer system. Components 312 and 350 may be implemented as depicted in FIG. 1 with sequencing instrument 12 and computers 30. Certain components of system 300 may be optional.

A pre-processor 305 can process raw intensity values in embodiments that include pre-processing. For example, such pre-processing can remove cross-talk from the signals. Herein, intensity values can be raw or processed. A pre-processor can exist at any place in system 300 where raw intensity values are obtained. The intensity values can be obtained by sequencing nucleic acids of a training sample.

Initial basecaller 310 can receive raw or processed intensity values (e.g., light or electrical signals) for a training set and output initial base calls as initial sequences. Certain nucleic acids of the training sample may be selected for inputting measured intensity values to initial basecaller 310. For example, nucleic acids may be selected from various training samples and sequencing runs. Initial basecaller 310 outputs initial sequences for the nucleic acids. The sequences can include no-calls.

Initial basecaller 310 can use any basecalling algorithm. For example, a simple algorithm of calling the base corresponding to the maximum intensity value can be used. In one embodiment, a basecalling model from a previous iteration may be used for initial basecaller 310. A purpose for obtaining the initial sequences can be to determine the assumed sequences for training the model. Parameters for initial basecaller 310 can be set to favor high accuracy, which may lead to more no-calls, but can provide higher accuracy for calls that are made. As call rate is not so important for the initial basecaller, no-calls can be more tolerable.

Filter 320 can select specific initial sequences for future operations in the pipeline. In one implementation, the filtering can identify initial sequences that may be difficult to determine the corresponding assumed sequence. For example, if the initial sequence includes short tandem repeats, it may be difficult to determine the true sequence of the nucleic acid, as it may be difficult to correctly map the initial sequence. Thus, it may be difficult to identify errors in the initial base calls.

Filter 320 can also identify initial sequences including positions having low quality scores. For example, the intensity values for position may all be relatively low, which may or may not result in a no-call. Also, the top two intensity values may be relatively close. Filter 320 can reject initial sequences for too many no-calls (i.e., above a specified amount), or initial sequences having too many base calls of questionable accuracy. The specified amount can be dependent on positions of the initial base calls with quality scores below a threshold, e.g., too many consecutive, total, or per specified number of bases. Mirrored reads (due to the effect of the neighbors) can also be filtered out. Mirrored reads can occur when a location in an ordered array is empty or has relatively few templates of the target nucleic acid (thus, a weaker signal), and thus can mirror the signals from a neighbor. These mirrored reads can be removed when there are a significant number (e.g., determined using a cutoff) of base calls that reflect the base calls of a neighbor.

Mapper/Assembler 330 can receive filtered sequences from filter 320. Module 330 can perform mapping and/or assembling. A mapping function can map the filtered sequence to a reference sequence, allowing for some mismatches and/or mapping of no-calls. In one implementation, bases can be inserted at a no-call position to create a kmer that can be used to identify a matching k-mer in a reference index. In some instances, the portion of the reference sequence to which the filtered sequence is mapped can be identified as an assumed sequence for the corresponding nucleic acid. Thus, if there is a mismatch in the mapping of the filtered sequence to the reference, an error in the initial base calls would be identified. The corrected assumed sequence can be used by a training algorithm, which can lead to the resulting basecalling model avoiding the error.

The assembling function can analyze the filtered sequences to identify sequences that overlap. These overlapping sequences can be used to determine a consensus sequence in a region corresponding to a particular filtered sequence. The consensus sequence can be taken as the assumed sequence of the corresponding nucleic acid. Any suitable technique for assembly may be used. A post-mapping assembly or a de novo assembly can be used.

Filter 335 can identify entire assumed sequences to remove or portions of assumed sequences that are not to be used in the training algorithm. For example, an initial sequence may include a no-call, but the assumed sequence can include a base at the position of the no-call. This may result when the initial sequence is mapped to a reference, and the assumed sequence includes the base at a no-call position of the initial sequence. It may be desirable not to use intensity values at the no-call position in the training (e.g., due to possible inaccuracy), and thus the assumed sequence can be modified to reapply the no-call at that no-call position. Other embodiments can keep the no-call position so that the model might be able to call a base when similar intensity values are encountered during a production run.

Filter 335 can remove assumed sequences that are not very reliable. For example, the initial sequence may map to the reference sequence, but with too many mismatches. Mapper/assembler 330 can also identify such instances, and thus no assumed sequence would be generated for the corresponding nucleic acid. Further, if the mapping shows characteristics of a chimeric sequence, then the sequence can be removed. For example, mapping mismatches of greater than 40% or 50% (e.g., 3 errors out of 5 consecutive positions) can indicate that the sequence is the result of biochemical problems during the sequencing process. Given that the goal is to perform accurate training, there is not a need to obtain sequencing information for every nucleic acid. Thus, judicious decisions can be made in filters 320 and 335 to identify assumed sequences that are accurate. The amount of bad sequences that are thrown out or portions of sequences that are not used in the training can be monitored so that biases to not result. Such biases might result when the filtering causes the training set to no longer be representative of the samples to be tested.

Training module 340 can use the assumed sequences from filter 335 and corresponding intensity values (raw or processed) of the training set to determine the parameters for the basecalling model. Training module 340 can include an optimization technique that minimizes differences in the output basecalling model from the assumed sequences. Thus, training model 340 attempts to determine parameters for the model that would result in the output of the model being the same or nearly the same as assumed sequences when the measured intensity values are input to the model. Various optimization techniques can be used, such as gradient descent, Gauss-Newton, Levenberg-Marquadt, conjugate gradient, and others. Once the basecalling model has been determined, it may be implemented in a production run. Basecalling parameters can define a basecalling model 350. Examples of basecalling parameters are weights and structure of a neural network, or a definition of a hyperplane for a support vector machine.

In a production run, nucleic acids are provided to sequencing instrument 312, which can output new intensity values for positions of nucleic acids from the new sample. These intensity values (raw or processed) can be input to basecalling model 350, which can provide base calls determined using basecalling parameters that are consistent with the training. Basecalling model 350 can be iteratively improved, e.g., by using the output base calls as a new training set. This is depicted as the dashed line 360 providing a new set of initial sequences to filter 320. Dashed line 360 effectively uses a previous basecalling model as an initial basecaller as part of an iterative refinement.

B. Method

Figure 4:
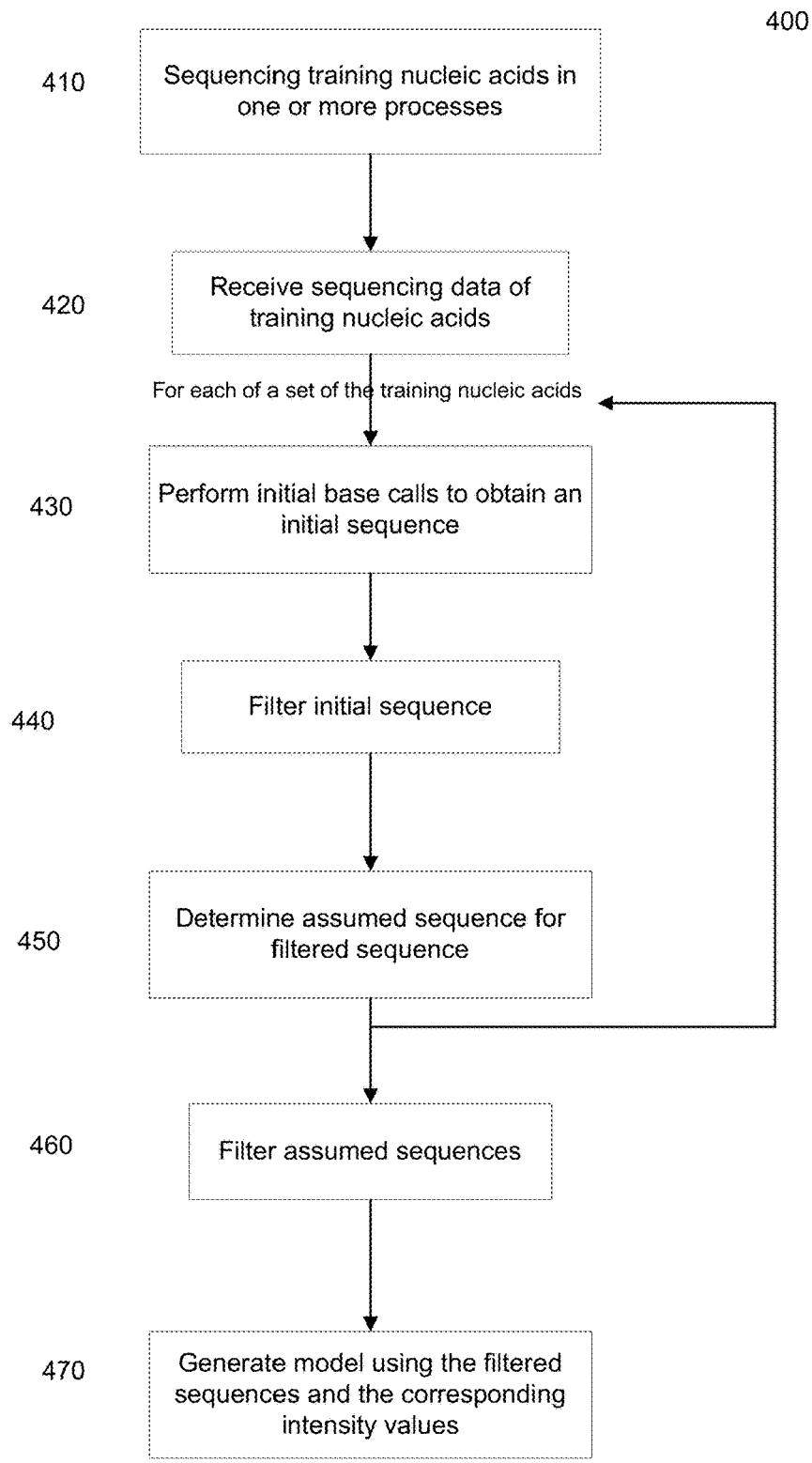
FIG. 4 is a flowchart of a method 400 of creating a basecalling model according to embodiments of the present invention.

FIG. 4 is a flowchart of a method 400 of creating a basecalling model according to embodiments of the present invention. Various blocks of method 400 can be performed at different times and by different entities. Parts of method 400 can be optional. Method 400 can be performed entirely or partially by system 300.

At block 410, one or more sequencing processes are performed on one or more training samples that include training nucleic acids. A plurality of training nucleic acids can be sequenced during each of the respective sequencing processes. The training nucleic acids in one sequencing process can be the same organism or from different organisms, and the training nucleic acids of different sequencing processes can involve different organisms. The sequencing of the training nucleic acid can sequence all or just a portion of the training nucleic acid. Sequencing of a training nucleic acid provides intensity values for bases at positions of the training nucleic acid. As examples, the sequencing data can be: one intensity for each base, multiple intensity values per base, or fewer intensity values than bases. The sequencing process used for training is ideally the same process as used for production runs.

At block 420, a computer system receives sequencing data of training nucleic acids from the one or more sequencing processes of one or more training samples. The sequencing data includes intensity values for bases at positions of the training nucleic acids. The sequencing data can correspond to all the training nucleic acids that were sequenced or just a portion of the training nucleic acids. Thus, the sequencing data can be filtered to identify a set of the training nucleic acids to use in generating the model. For example, a specified amount of sequencing data from each sequencing process can be used. As examples, the specified amount can correspond to at least a minimum number of nucleic acids for each sequencing process, and can be less than a maximum number. The specified amount can be expressed as a percentage.

Blocks 430-450 can be performed for each of a set of the training nucleic acids.

At block 430, an initial base call is performed at positions of the training nucleic acid to obtain an initial sequence. Initial base calls are based at least on the intensity values at the positions of the training nucleic acid. As described above, the initial base calls can be performed in any suitable manner, and can be single-cycle or multi-cycle, use intensities from neighboring nucleic acids or not, etc. The initial base call can include a no-call. The set of training nucleic acids can include all of the training nucleic acids for which sequencing data is received, or just a portion.

At block 440, the initial sequence can be filtered to remove the initial sequence or modify particular base calls in the initial sequence. The decision as to whether to discard or modify an initial sequence can be based on various criteria. As mentioned FIG. 3, an initial sequence might be discarded if the initial sequence has low complexity, e.g., includes repeated bases or short tandem repeats. As another example, the filtered set can be selected to achieve a specified GC content for the set. Other criteria for selecting initial sequences to use can include: undersampling low complexity regions, undersampling prevalent sequences in the genome, and oversampling rare sequences. Discarding can be accomplished in a hard or a soft way, e.g., with a soft discarding using weights to reduce a contribution from less desirable positions or initial sequences, where a weight of zero at a particular position would completely discard that position.

Besides discarding, initial sequences can be modified. Examples include substituting bases for position where there is a no-call, which can allow for better mapping, particularly when the mapping is accomplished using an index. U.S. Patent Publications 2010/0286925, 2010/0287165, and 2011/0015864 provide further details on mapping using an index. U.S. application Ser. No. 14/467,797 provides further details regarding indexes. These publications and application are incorporated by reference. Block 440 is optional.

At block 450, an assumed sequence corresponding to the filtered sequence is determined. The filtered sequence may simply be the initial sequence. If the initial sequence is discarded, then no assumed sequence would be determined. The assumed sequence is assumed to be the correct sequence for the positions of the training nucleic acid. The assumed sequence may be determined in various ways, including using mapping and/or assembly, or by voting among different types of initial basecallers.

At block 460, the assumed sequences are filtered to obtain a set of filtered sequences. The filtering can remove all or a portion of at least one of the assumed sequences. As described above, various criteria can be used for this filtering. For example, certain bases in the assumed sequence can be masked so that they are not used in the training of the model. The assumed sequence can also be discarded if it cannot be determined with sufficient accuracy, e.g., if the initial sequence maps to several locations in a reference sequence or only maps with too many mismatches. As another example, if a polymorphism (e.g., a SNP) is known to occur at a particular position, then that position can be discarded from being used in training the model. Discarding can be accomplished using weights to reduce a contribution from less desirable positions or assumed sequences, where a weight of zero at a particular position would discard that position. Block 460 is an example of a block that is optional.

At block 470, the basecalling model is generated using the filtered sequences and the intensity values corresponding to the filtered sequences. The basecalling model can be generated in various ways. For example, the basecalling model can be defined by parameters that are determined through an optimization process. In the optimization process, an initial estimate can be made for the parameters. More than one initial estimate can be used, and the resulting model that best fits the data can be used. For instance, the model that provides the fewest errors in the predicted base calls based on an input of the intensity values can be used. The use of multiple initial estimates can avoid being stuck in a local minimum, which would provide an inferior model. As a model can be generated for relatively long period of time using data from separate sequencing processes than one used in a production run, one can allow an extended optimization process to achieve a best model.

C. Training Samples

As mentioned above, multiple training samples can be used. The training samples can be taken from various organisms and can be chosen to provide a representative set of nucleic acids. The representative set should be similar to nucleic acids the model will ultimately be used for base-calling. Various training samples can be chosen for different properties. For example, one training sample might be chosen because the sequences are artificially made and therefore known ahead of time. Another training sample might also be chosen because the nucleic acids have a particular property, e.g., having a particular GC content.

The number of assumed sequences of nucleic acids used to provide a representative set can depend on the training samples used and whether the model has previously been trained. For example, the model can be updated using a new set of training nucleic acids, where the parameters of the old model are used as the initial estimate for the parameters of the new model. The number of assumed sequences can be smaller when a model is being updated as compared to when the model is first created. Also, the size of the training set may be determined by comparing the level of discordances or errors observed in the initial basecaller, which may be an older version of the model. The new set of training nucleic acids can be from a new production run.

1. Artificial Sequences

In one embodiment, the training nucleic acids can include artificial sequences, for which the sequences are known. Since the sequences are known, the assumed sequence can be determined with high accuracy. The set of artificial sequences can be chosen such that any one of the sequences differs from another artificial sequence by a least M bases. In this manner, the likelihood is small that errors in initial base calls would cause an incorrect sequence to be identified as the assumed sequence. As long as the number of errors is less than M/2, the correct sequence can be identified, since it would be the artificial sequence that is most similar to the initial sequence. The set of artificial sequences can include Reed-Solomon codes.

In one implementation, the artificial nucleic acids can be a barcode, which may be attached to nucleic acids from an organism. For example, a barcode can be added to an end of the nucleic acid. The barcode can be used to identify which aliquot a nucleic acid is from. When the combined nucleic acid (i.e., artificial part and part from the organism) is sequenced, an initial determination can be made for both the artificial sequence and the natural sequence of the organism. In this manner, fewer sequencing runs may be needed.

The determination of the assumed sequence for the artificial nucleic acid can be performed using a look-up table. Since the length and the content of the artificial sequences are known, a table can be created of the artificial sequences. This table can be searched using an initial sequence to identify the correct sequence that corresponds to the initial sequence. For example, the initial sequence can include one error, and the assumed sequence can be identified as a sequence of the table that is most similar to the initial sequence.

A drawback of using artificial sequences can be that the number of artificial sequences may not be large enough to provide a good representative sample. For example, the structure of the artificial sequences may not be varied enough to provide a good representative sample. This can be the case when error-correcting codes are used as the artificial sequences, since the codes dictate a structure of the artificial sequences. Thus, it may be difficult to produce an accurate statistical distribution of different sequences, such that the training set mirrors the proportions of sequences in an organism. Potentially, if there are millions of different artificial sequences, then the representative sample might be sufficient. For example, the set of artificial sequences can include sequences that are similar to actual sequences of an organism. But, the preparation of that many artificial sequences can be difficult.

To provide more sequences, when error-correcting codes are used, random artificial sequences (or at least non-correcting sequences) can be physically attached to the codes. Although there may be a limited number of error correcting codes, each code could have different a non-correcting sequence added per lane. As another technique for combining different types of sequences, artificial sequences can be used for one training set, and then genomic sequences can be used in a subsequent training set, which is used to refine the model. Or, both artificial sequences and genomic sequences can be used in the same training set.

2. From Organism

As described herein, nucleic acids from an organism can be used as a training sample. For example, genomic DNA can be used. The genomic DNA can be sequenced, and an initial sequence can be determined. Mapping and/or assembly can be used to determine the assumed sequence corresponding to a DNA fragment. Using genomic DNA from a same type of organism (e.g., human or broader to be any animal) can help to provide a representative training set.

Such a training sample can be selected from a person whose genome has been accurately determined previously. Using a known genome can help to increase the accuracy of the assumed sequences. But, using a known genome is not necessary since assumed sequences can be still determined for other samples, as described herein. Different training samples can also be chosen for different populations. In this manner, different models can be generated for different populations.

3. Different Organism

It is also possible to train the model on one type of organism, and implement the model on a different organism. For example, a bacterium (e.g., E. coli) can be used to train the model, and then the model can be used to determine base calls for nucleic acids from humans. Bacteria are suitable for this purpose as they are uniploid and have only one chromosome. Thus, the reference genome of the bacteria can be determined accurately. This accuracy can help to determine the assumed sequences more accurately, e.g., because it is easier to map to a uniploid organism with only one chromosome. Whereas, mapping for humans is more subject to errors.

However, a single bacterium may not have the variety of different sequences that may occur in more complex organism, such as a human. Thus, multiple bacteria (or other small organisms, such as a phage) can be used as training samples. In this manner, the genomes of the multiple bacteria can collectively represent the complexity of the human. For example, the bacteria can be chosen to cover a wide range of GC content that is seen across chromosomal regions of the human. For instance, the GC content on E. coli is about 50%, and on humans it is about 41%. A combination of bacteria can provide a more representative training sample with regards to GC content, e.g., by combining E. coli with other bacteria that have less than 41%, thereby providing an average of 41%.

Bacteria can also differ, e.g., by the type and number of repeat regions, as well as a location of the repeat regions. A combination with other organisms can fill in the gaps by utilizing sequences having specific repeat behavior. Thus, specific parts of the genome of another organism can be chosen to include in a training sample because the specific parts have desirable properties similar to the organism for which the model will be used.

4. Using Multiple Samples

As mentioned above, training samples from various sources can be used together in generating the model. For example, artificial sequences can be combined with actual genomic sequences to obtain a better representative set. Each sample can undergo an independent mapping and/or assembly to determine an assumed sequence.

In one embodiment, the multiple samples can effectively be combined by training on a first sample to obtain a first estimate of the model, and then refining the first estimate by using a second sample. Thus, the samples can be used to train the model separately. The first sample might be artificial sequences of the genome of a small organism, which can provide good initial accuracy for many common sequences, although not providing the desirable breadth. The second sample can then include a human sample, which can provide the additional complexity to realize a good representative sample for humans.

5. Multiple Slides

Besides using training samples from different organisms, training samples can be used in multiple sequencing runs. Each sequencing run can include samples from different organisms of the same type, different types of organisms, and even samples from the exact same organism (e.g., from the same person). Each sequencing run can use a different slide (substrate), e.g., a different object but made of the same material. Different sequencing runs can produce different variations in optics and biochemistry for various reasons. Thus, the combination of different sequencing runs can provide representative set that accounts for variations that might occur in production runs.

In some embodiments, not all of the sequencing data from a single slide might be used. Since there is a budget of time for training, it might be prohibitive to use all the data from all the slides. Thus, a subset can be selected from each slide, e.g., a few million sequences from each sequencing run. The selected sequences can also be taken from different parts (e.g., different lanes) of different slides, potentially with a subset selected from the nucleic acids of each part of a slide. The selected sequences can be selected randomly or in a predetermined manner.

The selected sequences can also be chosen such that a good representation is provided for each part of the genome. Sequences that occur more often also be selected more frequently. For example, k-mers that occur often in nature may be chosen more than k-mers that rarely occur. However, the selection might ensure that enough rare k-mers are selected to provide sufficient accuracy.

Thus, a preferable selection for common k-mers can provide more accuracy for the most common sequences. But, after a certain point, more data may not improve the model much after a sufficient amount of data is used. Therefore, given a limited budget for the number of training nucleic acids, rare k-mers can be used in a greater percentage than might occur naturally, but still at a lower absolute rate than more common k-mers.

D. Initial Base Call

The algorithm for the initial base call can be conservative in order to provide accurate base calls. It is not necessary to determine an entire genome as part of the training, as the training nucleic acids are simply there for training purposes and not for investigating the particular organism from which the training nucleic acids were obtained. Accordingly, parameters for the initial basecaller can be chosen to obtain accurate base calls at the expense of more no-calls. For example, a minimum intensity or score can be required for a base to be called. The minimum value can be set relatively high, e.g., while ensuring that no bias is introduced.

The chosen parameters may also cause the initial basecaller to be slower, which is not detrimental as the training is done for training-specific sequencing runs. That is, it can be defined to be slower but more accurate in such instances.

In one embodiment, multiple initial basecallers may be used. The consensus among the various initial basecallers can be used as the base call. The various basecallers can vary by the algorithmic technique or by having different parameters for a same algorithmic technique.

Examples of initial basecallers includes using an overlap in the wavelength spectrum between the different signals of the different bases. A crosstalk matrix can be used to correct the intensity values. Another example includes using a statistical function to address the variations in the amplification of a template, e.g., different sizes in a cluster or nanoball.

E. Determining Assumed Sequence

Ideally, the model determines the correct base calls based on intensity values. To this end, the assumed sequences used for training should be accurate. The determination of the assumed sequences can be performed (but not limited to) any the following methods: (1) Use artificial sequences and use the decoded sequences as the expected outputs; (2) Use real nucleic acids and use the reference sequence of the mapped sequence as the expected outputs; (3) Use real nucleic acids and use the assembled consensus sequence from the initial sequences as the expected outputs 1. Decoding The decoding of an initial sequence to correspond to an unknown artificial sequence can be performed in various ways. In one embodiment, a table can include the artificial sequences. The table can be organized for more efficient searching. For example, the table can be organized alphabetically or by some other rubric that provides an order among the four bases. When initial sequences are received, the table can be searched such that each base position is used to identify potential matches. The potential matches can be identified using the organization of the table. For instance, all of the artificial sequences starting with an A can immediately be identified as the first 25% of the artificial sequences listed in the table. Each additional base can reduce the potential matching artificial sequences by 25%. Thus, the initial sequence does not need to be compared in its entirety to each artificial sequence table.

It can happen that an exact match is not found. For instance, every possible combination of bases may not exist in the table. The artificial sequences can be constructed such that they are not too similar to each other, e.g., they may be required to differ by three or more bases so that errors can be corrected. If there is no exact match, the most similar artificial sequence (e.g., the one with the fewest number of different bases) can be identified as corresponding to the initial sequence. In this manner, the initial sequence has been decoded to be the artificial sequence that is closest. Then, the closest artificial sequence can be taken as the assumed sequence.

2. Mapping

The assumed sequence can also be determined by mapping the initial sequence to a reference sequence. This would generally apply to when the training nucleic acids are nucleic acids from an organism. The reference sequence can correspond to a known sequence of a particular individual. If the initial sequence maps exactly to a unique location in the reference sequence, then the initial sequence can be identified as corresponding to the assumed sequence, since there are no errors. However, there can be one or more mismatches in the alignment of the initial sequence to the reference sequence, i.e., mismatches for the location that provides the best alignment of the initial sequence to the reference sequence. The initial sequence may have no-calls, and the alignment can fill in those gaps with the bases from the reference sequence at the aligned location.

When there is a mismatch in a particular base position between the initial sequence and the reference sequence at the location of best alignment, the mismatched base position can be identified as an error in the initial base call. For example, the initial sequence can be 24 bases long and aligned to the reference sequence with one position that has a mismatch. The one position could have an A in the initial sequence and a G in the reference sequence. Given that the initial sequence otherwise uniquely aligns to the one location in the reference sequence, the reference sequence with the G can be taken as the assumed sequence. In a similar manner, a no-call at the one position can be converted to a G for the assumed sequence. In some embodiments, the conversion to G can be limited to positions that are not know to be SNPs.

Issues could arise if the mapping is incorrect. To avoid incorrect mappings, training nucleic acids from one organism with a simpler genome can be used, as described above. Using a simpler genome that is uniploid and with relatively few chromosomes (e.g., one), as well as having a smaller total length, can facilitate a mapping procedure. For example, such a simpler genome can result in fewer multiple mappings.

Additionally, parameters for the mapping procedure can be chosen to provide high-quality mapping. For example, a threshold for the number of mismatches that are allowed for alignment can be relatively low, such as only 2-4 mismatches. Also, if two locations in the reference sequence align with the same number of mismatches (but in different positions of the initial sequence), then that initial sequence can be discarded (filtered). Such a filtering can be performed by filter 335 of FIG. 3. Other examples include filtering out the sequences that have low entropy, that are repeated on the genome (which can reduce trust in mapping), that map non-uniquely on the genome, that have low basecalling score (e.g., as compared to a threshold) for a specified number of positions (e.g., more than 50% of the positions), and those that are clonal reads or otherwise duplicated reads. The filtering can eliminate (e.g., hard or soft via weighting) any position of a sequence (or the entire sequence) that might cast doubt about the quality of mapping and therefore result in incorrect base calls for training.

As another example, the initial sequence can be modified to identify the best matching location, and therefore the best assumed sequence. This modification can identify base positions that are of a low-quality, and thus may be inaccurate. These base positions can effectively be masked from the mapping procedure, so that a mismatch is not counted. The masking can be performed in various ways, e.g., each of the four bases can be inserted into the base position and each attempted to align to the reference sequence, where the alignment can utilize a reference index. These modifications can be performed with filter 320 in FIG. 3.

The mapping procedure can also account for where the mismatches occur. For example, if the mismatches occur in consecutive positions, then a different threshold (potentially lower) might be used for whether or not the mapping is used to determine the assumed sequence. Also, if the consecutive positions are at the end of the initial sequence, a different threshold can be used than if the consecutive positions were within the initial sequence (e.g., near the middle of the initial sequence). A threshold can also be used for minimum number of mismatches per N bases. For example, the number of mismatches in any stretch of 10 bases can be required to be less than two or three.

Consecutive mismatches can result from errors in a sequencing process, as may occur in amplification reactions and sequencing reactions. For example, part of one nucleic acid from one part of the genome can be combined with another nucleic acid from a different part of the genome, thereby creating a nucleic acid that does not correspond to the actual genome of the organism. Also, consecutive mismatches can indicate an indel, which also may result from library preparation. An indel might also reflect the actual genome of the organism, but due to difficulties in determining the correct sequence, an initial sequence with an indel can be discarded in order to preserve accuracy of the training data. The mapping procedure can also identify multiple initial sequences that have similar errors, which is indicative of errors in the biochemistry of the sequencing process. Such similar errors may be confined to consecutive errors, such that actual polymorphisms are not discarded. However, other implementations may seek to discard initial sequences that reflect actual polymorphisms in the organism.

The mapping can include both arm reads of a mate pair of a single nucleic acid. For example, two ends (e.g., 20-500 bases) of a DNA fragment can be sequenced, where the DNA fragment is several hundred bases long. Given that the two arm reads are from the same DNA fragment, the arm reads should map to locations in the reference that are relatively close to each other (e.g., within a specified threshold, such as 1,000 bases). The number of mismatches per arm can be used as a criteria as to whether or not to accept an alignment to a particular location.

If a particular base position was found to have low quality or be a no-call, an alignment can occur for a base at the position reference, as mentioned above. However, such a base position can be excluded from training. Thus, the assumed sequence corresponding to the initial sequence can still be used; therefore avoiding a bias from excluding such sequences, and the accuracy can be preserved by not including such low-quality base positions. Additionally, if two bases (or other number of bases) at a particular position have similar scores then both bases can be used in determining a mapping to the reference.

3. Assembly

Instead of or in combination with mapping, one can use assembly to determine the assumed sequence. An assembly procedure can include comparing initial sequences to each other to determine a consensus sequence, which may include polymorphisms if the initial sequences provide sufficient support. The consensus sequence can be determined by identifying overlapping parts of different initial sequences. The part of the consensus sequence corresponding to a particular initial sequence can be used as the corresponding assumed sequence. The assembly can include de novo assembly and/or local de novo assembly.

A consensus sequence of the initial sequences can be determined after mapping. For example, the initial sequences can be mapped to the reference, and the initial sequences that align to a same region of the genome can be assembled to determine a consensus sequence. Such techniques can be referred to as post-mapping assembly. Examples include www.broadinstitute.org/gatk/guide/best-practices and soap.genomics.org.cn/.

Combining assembly with mapping may be of a particular advantage when the region includes an indel or other variation from the reference. The separate process can help to distinguish between an indel and an SNP, thereby providing more accurate assumed sequence. In this manner, initial sequences that might have otherwise been discarded can still be used by performing assembly to determine the assumed sequence corresponding to an initial sequence, which might have significant variation from the reference. The region for assembly can be as small as one base, and thus the assembly can identify SNPs. Thus, a base position corresponding to a SNP can be preserved for training purposes, which can provide a better representative sample for training.

If assembly is used without mapping, it can be difficult to know which initial sequences overlap with other initial sequences in the genome corresponding to the training sample. Long fragment read (LFR) technology can be used to reduce the subset of initial sequences that are compared to each other to determine a consensus sequence for a particular region. Details of LFR and assembly can be found in U.S. Pat. No. 8,592,150, U.S. Publication 2013/0096841, and U.S. application Ser. No. 14/467,797. If the training sample corresponds to a small organism (i.e., a small genome), then assembly may be more feasible without using LFR techniques. Another example of de novo assembly can be found at res.illumina.com/documents/products/technotes/technote_denovo_assembly_ecoli.pdf.

F. Filtering

As described above, the initial sequences in the assumed sequences can be filtered (e.g., discarded or modified) to achieve more accurate training data. For example, nucleic acids that show excessive variations (e.g., structural variations) can be discarded, as there is a high likelihood of error. Additionally, if an initial sequence maps to a particular part of the genome, the initial sequence can be excluded. However, excluding sequences from a particular part of the genome can cause inaccuracies basecalling for nucleic acids from such a region. Also, as mentioned above, the quality score of a base on the initial call can be required to be of a sufficient level for the base to be used. This can ensure a greater accuracy for the training model. But, this can limit the model in handling base calls with low quality scores. The quality of all of the bases of the initial sequence can be analyzed collectively, so that some low quality bases can be acceptable, but not too many.

1. Polymorphisms

Difficulties can arise in determining the assumed sequence of a training sample having a polymorphism (e.g., SNP or other variation) relative to a reference sequence. Such variations can cause the correct base call to be changed into an incorrect base call when a reference sequence is taken as the assumed sequence after mapping. The filtering can identify such base positions and remove such base positions from the training data, allowing other positions in the initial sequence to be used for training. Although the mapping would typically provide a correct base call, a small but not insignificant percentage (e.g., 0.1%) of the mismatches in mapping might be attributable to a variation in a genome corresponding to the training sample. Local assembly can help to avoid such errors by identifying consistency across initial sequences that map to the location of the variation, as mentioned above.

As mentioned above, if there is evidence of an actual variation, then that position can be excluded from the training data. Genomic positions that are known to include variations can be used to exclude base calls corresponding to those positions, thereby avoiding possible errors. Such a library of variations includes the single nucleotide polymorphism database (dbSNP). The library variations can also be used in the mapping process to modify the initial sequence to have either one of the two prevalent alleles at a position. It can be determined whether or not to use such modified positions in the training data. If a specific individual's genome (or a set of individuals) is used for training, the loci corresponding to variation sites (e.g., SNV, Indel, structural variation (SV)) can be filtered out. Thus, any read or portion of a read that maps to those regions can be excluded from the training set. Besides removing, the location of a variation can be used in other ways. For example, a flag could identify a variation, where later processing can use the flag to not use the location for a particular step. Or, a weight can used to limit all or some contributions from the location for all or some reads.

2. Entropy

The filtering of the initial sequences and the assumed sequences can use the content of the sequence to determine whether or not the sequence should be discarded. For example, sequences that have low complexity might be difficult to map, and thus may be discarded since it can be difficult to determine a correct assumed sequence. Sequences with low complexity include sequences having many repeats of a particular base, or tandem repeats and homopolymers. Such sequences can be difficult to map.

The mapping procedure can mask repeats, but then computational cost is still expended in attempting to map to the reference. And, an initial sequence having low complexity might still map to an incorrect location. Instead, the filtering (e.g., by filter 320) can identify initial sequences that have low complexity (entropy) and discard those initial sequences before mapping is even attempted.

The level of complexity needed to send the initial sequence to the mapping procedure can be based on an expected error in the mapping due to the level of complexity. If the expected error is above the threshold, then that complexity can be deemed insufficient, and the initial sequence can be discarded. In this manner, the bias for discarding initial sequences can be controlled, such that minimal bias is introduced only when the expected error is higher than an acceptable threshold.

The level of complexity can be measured as a probability of encountering the sequence if it was generated randomly. The level of complexity can be combined with other factors (e.g., quality scores of initial base calls) for determining whether to discard an initial sequence.

Such a filtering and mapping process would have distinct disadvantages as a commercial mapper for actually determining a genome of a sample. However, such a filtering and mapping process is suitable for training the model.

IV. Use of Model

Once a model is trained, the model can be used in a production run. During the production run, there would be no initial basecaller or determination of an assumed sequence. Instead, the model is used to determine the base calls. Once the base calls are determined, mapping and assembly procedures can still be performed, e.g., to identify variations from a reference or to determine an entire genome, or at least a large part of the genome.

A. Input

In one embodiment, the input is a matrix of M×N intensities, where M is the number of color planes that are acquired (e.g., M=4 for most DNA sequencing technologies, with one color planes for each of the four bases), and N is the number of the base positions that are considered simultaneously (e.g., 10 in a multi-cycle scheme). N can equal the number of positions (cycles) in a nucleic acid that contribute to a given position. For example, N can be three, such that intensities from the current cycle and two previous cycles are used as input. In another embodiment, if P neighbors are considered, then the matrix can be M×N×(P+1). The intensities of the neighbors can be chosen to only be for the current cycle as well, and thus the total inputs would be M×N+M×(P+1). Since the neighbor intensities from the current cycle would generally have the most impact on the base call for a given cycle, such inputs can be used when the output of a single operation of the model only provides a base call for the current cycle.

The effect of the neighbors can be summed up, so in any of the previous equations, P+1 could reduce to 1+1=2. Other methods of combination are also available. The neighbors could include the immediate (closest) neighbors and potentially the next closest neighbors. The neighbors could also be dynamically selected, e.g., those within a given radius in a random array.

The input intensities can be in various forms. Example intensities include: (1) raw intensities; (2) local background-subtracted values; (3) crosstalk-corrected values; (4) crosstalk-corrected and normalized values; (5) any of the above for the nucleic acids of interest and the neighboring nucleic acids; and (6) any allowable combination of the above. The input may be expanded to include positional neighbor information (e.g., X-Y location of a particular neighbor intensity) relative to the nucleic acid whose base is being called for a given position. The neighbor intensities can include the individual intensities or their aggregate intensities.

Due to the general nature of this training, the model lends itself to other basecalling schemes, e.g., where only two colors are used (as described herein) or two base positions are assayed in the same reaction (e.g., using two colors for each position). The overall method can remain unchanged, where the inputs will be 2×N as opposed to 4×N. If the information for all the 4 bases are included in the 2 intensities (e.g., using zero and positive intensities for the two colors to cover the 4 bases), they will be utilized by the neural network, in order to render the appropriate 4 scores for each position being called.

B. Output

As described above, the model can output a base call. In one embodiment, a model can also output (provide) scores for each base for a given position. A separate heuristic operation (e.g., taking a maximum) can be used to determine the base call from the scores. In one embodiment, the heuristic operation can be considered part of the model, where the part of the model that provides the score is trained with the training data.

In one implementation, an output of the model is an M×N matrix of scores (e.g., between 0 and 1), where each of the M values can represent the probability or possibility of the corresponding base to be present; and each member of N represents the base position of interest in the multi-basecalling scheme. The value of N for the outputs can be different than for the inputs. For example, N can be five for the inputs, such that five cycles of intensities are used to call a base of a given nucleic acid (e.g., the intensities of the current cycle and intensities of four previous cycles), but the output can be the scores of the bases only for the current cycle. Then, for the next cycle, the inputs would again be for five cycles of intensities, and the score only for the next cycle. In another embodiment, the N values can be the same, such that scores are output for multiple cycles at the same time. N can also be between 1 and the number of input cycles used. The values of N for input and output would be chosen before training the model.

The model can be a "possibilistic model" as opposed to a "probabilistic model." In a possibilistic model, the scores for the possible solutions do not necessarily sum to 1, although they may sum to 1. In other words, a base is not forced to be A, C, G, or T. Instead, it is allowed to be none. This allows a natural framework for capturing damaged nucleic acids or non-existing nucleic acids. At the same time, this model allows for multiple bases to be called (which is similar with a probabilistic model), and therefore does not force a single base call.

In one implementation, when using possibility scores, there is no need to capture behavior in a "score" via heuristics. As a corollary, multiple base calls can be made fairly easily. For instance, if the 4 possibilities for a certain base are (A=0.5, C=0.5, G=0 and T=0), then one could infer that the base call is A/C (A or C, each with 50% confidence). Moreover, a no-call can be made where all the possibilities are low, e.g., A=0.1, C=0, G=0.1, and T=0. A basecaller with the above characteristics is advantageous for a general purpose mapper, which can tolerate a large number of no-calls (Ns), potentially at random places. Accuracy can increase if doubtful bases are changed into Ns, as mapping to the correct sequence might have been prevented if a base call was wrong, whereas an N would not prevent the correct mapping. Thus, an advantage is that a possibilistic model does not force a base call to be made by having the scores sum to one.

In one embodiment, the input/output is for every five bases (or other number of bases), with five cycles worth of data, and an output of five bundles of calls. Each bundles of calls for a cycle can include scores for each of the four bases, or other number of bases as appropriate. In another embodiment, the model can have an input from N cycles (e.g., all pervious or for a window centered at the current cycle, such as +/−2 from current cycle) and an output for only one position, which can provide greater accuracy, but with a slower overall speed for basecalling.

A model can also be trained to output scores for more than one position of a nucleic acid for a single cycle. Thus, two bases can be called for a single cycle. By training the model to provide such output scores for two bases, a need for developing highly sophisticated Gaussian Mixture Models or other similar methods can be avoided. Even when two bases are determined per cycle, a traditional 4-color assay can be used. Even with these more complex inputs, the model can learn the patterns, as described herein.

C. Making a Call

As mentioned above, a score output by the model (or generated internally by the model) can be used to make a base call. For example, the base corresponding to the highest score can be called. If all the scores are low (i.e., below a threshold), then a no-call might be made. In other embodiments, the model can output a base call without using a score tied to a particular base, e.g., using a support vector machine.

The output scores for a given cycle can be used to call a base for the given position of the nucleic acid. The base call could include a single base call, a no-call, or a call of multiple bases, e.g., when sequencing data is input from multiple cycles or when a cycle includes data for multiple positions. As an example, C might have a score of 0.9, the other bases having scores of 0.3, 0.1 and 0.1. In this case, the highest score is 0.9, and C can be called for the given position. If none of scores are above a certain threshold or if the two top scores are sufficiently close, then a no-call might also be made. Thus, the model can include another layer of logic that uses scores to determine a base call. This other layer of logic can be considered to be separate from the model, or part of the model.

The scores can provide additional information besides how to make a base call. For example, a score may be above a threshold to make a base call, but one can know more about the confidence of the base call by having the score output. For example, a base call can be identified as having high confidence. Also, a base call can be identified as having low confidence, which may be useful in mapping and assembly procedures. Thus, a high calling rate can be achieved, while still providing additional information such that errors or inaccurate data is not propagated to future steps, such as phasing and assembly.

D. Calibration

In one embodiment, since the model can be trained to provide the same output for the same input, the output scores can be trained to not differ significantly from one production run to another. In other words, a score in one production run would signal the same level of confidence for the base call as the same score in another production run. Thus, the scores can be provided with uniformity from one sequencing run to another. For example, if the score is 0.5 for a base, the probability of the base being correct would be 50% for any instrument. Accordingly, a same threshold can be used.

For example, a threshold can preclude calling a base where there is below 95% probability. This 95% probability can be applied universally to other sequencing runs. The uniformity can be obtained due to the training of the model to provide uniform results.

In contrast, other techniques can provide rank or relative value between different bases, but a threshold for such a rank cannot be universally applied. For the other techniques, if the score is higher, oftentimes the probability is higher, but only on average because there is a confidence boundary. Thus, one knows a range of probabilities for given score, but there is not a known relationship.

Figure 5:
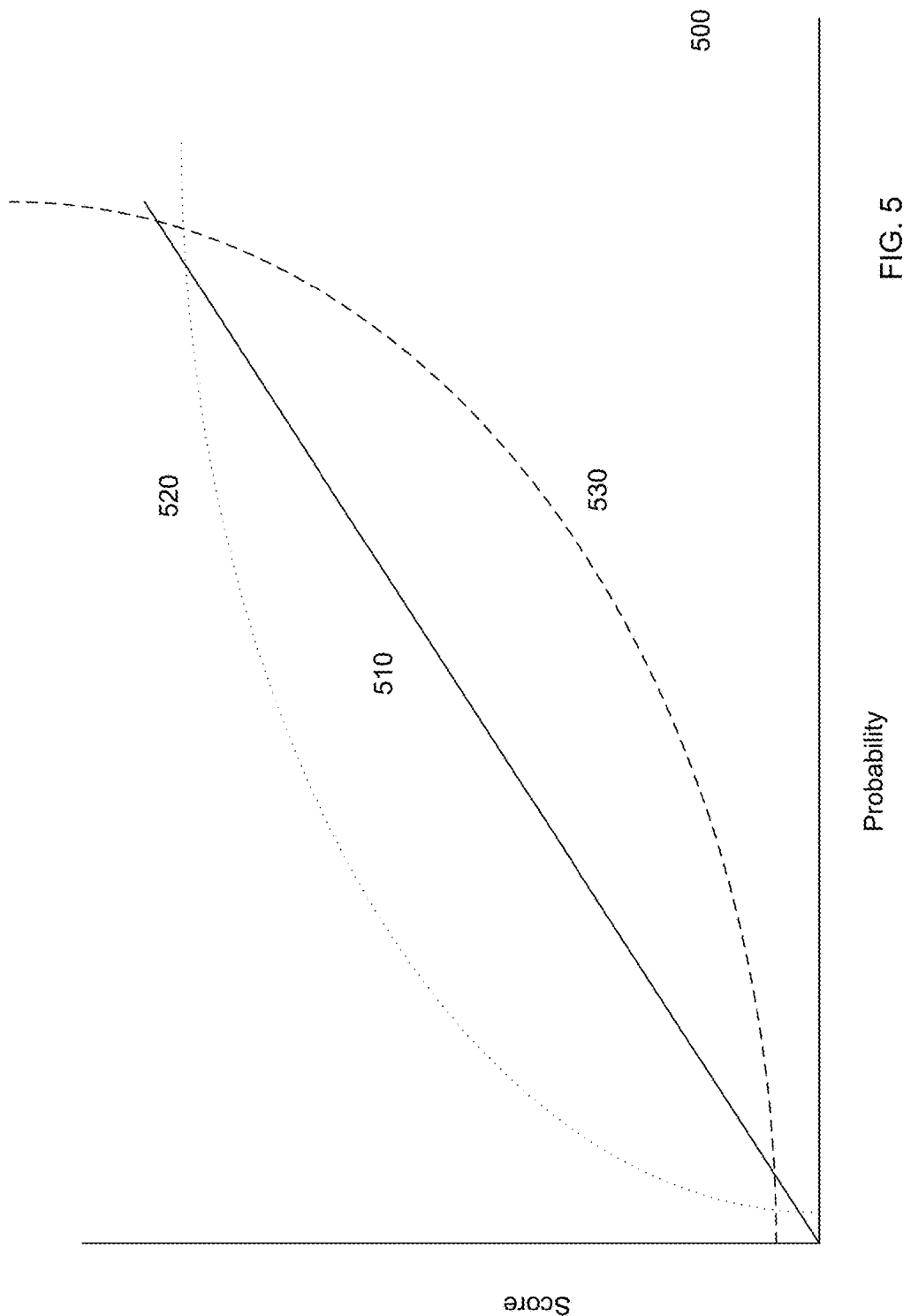
FIG. 5 shows a plot 500 illustrating a relationship between score and probability.

FIG. 5 shows a plot 500 illustrating a relationship between score and probability. The horizontal axis is probability and the vertical axis a score. Embodiments can provide a line 510 consistently across production runs. Line 510 provides a defined relationship between score and probability, e.g., an identity relationship with a 45 degree angle line. In contrast, techniques that provide a rank might actually have relationship corresponding to curves 520 or 530. In curves 520 or 530, an increase in score does increase the probability, but the relationship is different. Thus, a threshold for calling a base for one production run may not work as a threshold for another production run to call a base.

To address this problem, other techniques can perform a calibration step that identifies the relationship between score and probability. But, this calibration would be performed for each sequencing run, which adds extra work. Further, the calibration might need to be performed for different lanes and different fields of the same slide. Once the relationship is known, the curves 520 and 530 can be transformed into a line, e.g., one with 45° slope.

There is an advantage to not having to do any calibration during a run (or on a per run basis). The same thresholds can be used, and the process is more efficient. For example, less storage may be used. In calibration, much of the data needs to be collected in order to provide the calibration, and this data needs to all be stored. Whereas, embodiments of the present invention can make a base call with current data, and then proceed to discard that data. Further, this lower memory constraint allows the data to be stored in cache or other more efficient memory than a hard drive, which can significantly increase speed.

E. Method

Figure 6:
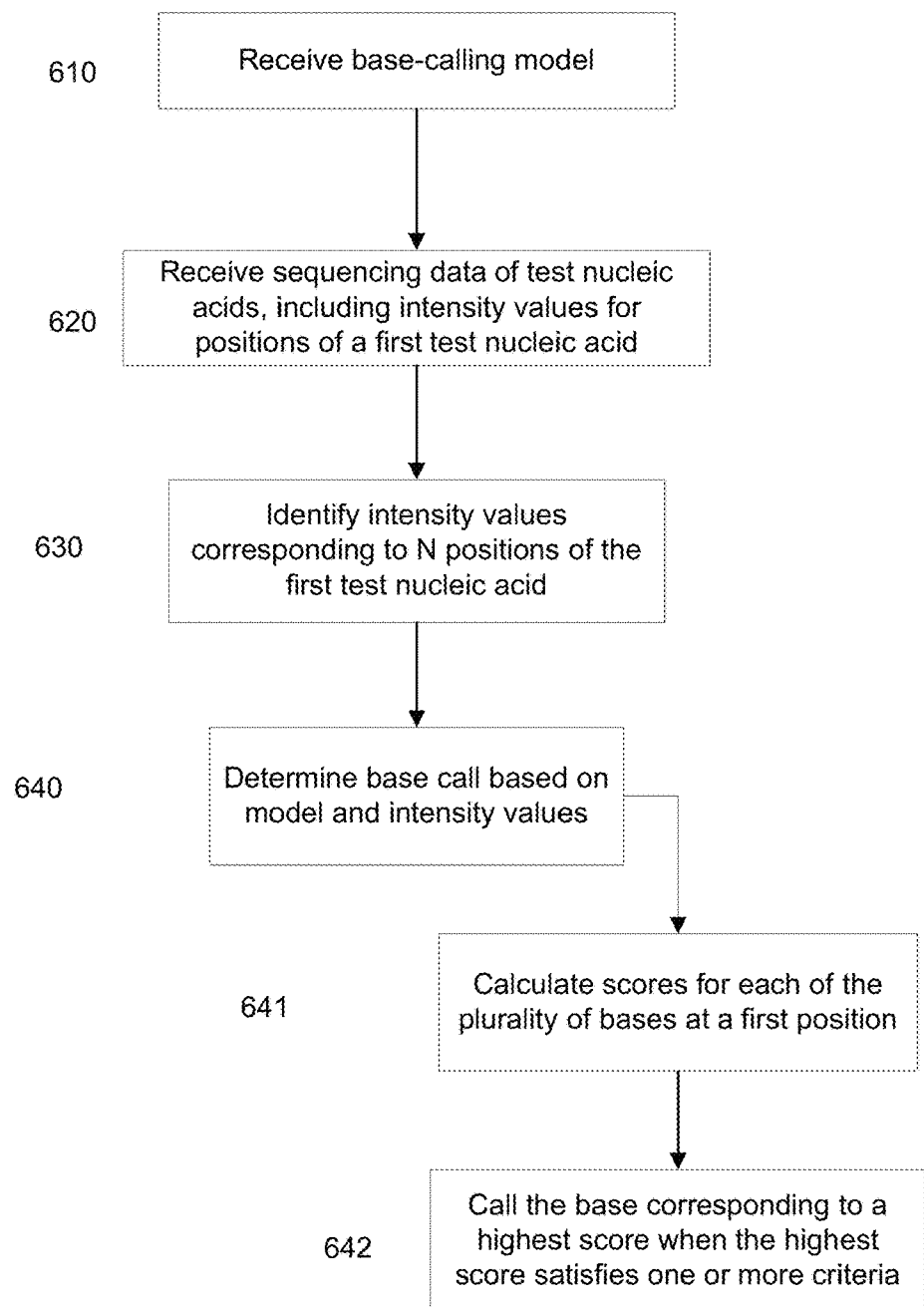
FIG. 6 is a flowchart of method 600 of calling one or more bases for a nucleic acid of an organism according to embodiments of the present invention.

FIG. 6 is a flowchart of method 600 of calling one or more bases for a nucleic acid of an organism according to embodiments of the present invention. Blocks 641 and 642 show an example of how block 640 may be implemented when the model generates a score for respective potential bases at a position, whereas other embodiments can output a base call directly. The basecalling model can include one or more pre-processing functions (e.g., modification of intensity values) and one or more post-processing functions (e.g., normalization of scores or use of a softmax function).

At block 610, a computer system receives a basecalling model. The basecalling model can be trained as described herein. For example, the basecalling model can receive inputs of intensity values for bases at one or more positions on a nucleic acid and can output a base call for each of the one or more positions. In one embodiment, the model can determine scores for each of the one or more positions. The base-calling model can be trained using a statistically significant number (e.g., at least 100, or at least 1,000, or at least 10,000) of assumed sequences of training nucleic acids, along with the corresponding intensity values for bases at the positions of the assumed sequences. The corresponding intensity values can be obtained from one or more first sequencing processes of training nucleic acids. The first sequencing processes can be performed using training samples on various slides.

At block 620, the computer system receives sequencing data of test nucleic acids from a second sequencing process that is different from any of the first sequencing processes. For example, the first sequencing processes can be performed weeks or months before the second sequencing process. The data from the first sequencing processes can be used to train the basecalling model. The sequencing data includes intensity values for bases at a plurality of positions of a first test nucleic acid.

At block 630, intensity values are identified for N (e.g., 1 or higher) positions of the first test nucleic acid. As examples, each intensity value can correspond to one base and one position. An intensity value can also correspond to multiple bases, e.g., when two colors are used to span four bases, effectively using both zero and positive intensities for both colors to cover four possibilities. An intensity value can correspond to more than one position, e.g., when an intensity corresponds to a doublet (two positions). That is, an intensity of a particular color channel can indicate a particular two-base combination. Different color channels would be analyzed for the doublet (or potentially higher number of positions). The number of bases could be 2-4, or more, e.g., if methylation of a base is counted as a different base. As mentioned herein, the intensity values can be raw values or modified values, e.g., by subjecting a background or other normalization.

At block 640, a computer system determines a base call based on the basecalling model and the intensity values. The intensity values for all the N positions can be used. The base call can be for one or more of the N positions. Base calls for all of the N positions can be obtained in the same function call. In one embodiment, the model outputs the base call. For example, a support vector machine (SVM) can output the base for the base call. In some implementations, no explicit score would be obtained with the base call. In other implementations, a score can be determined, where the score corresponds to a confidence in the base call. A confidence score can be determined as part of the model.

The confidence score may indicate how much more likely the called base is relative to another base being the correct base. For example, an amount of separation of a hyperplane for a support vector machine from the data points can be used to determine the confidence score. A data point can be a multi-dimensional point, with the value in each dimension being an intensity value for different base call. As another example, a data point can be a projection of the intensity values onto a multi-dimensional space. Other dimensions could correspond to other settings for the system, e.g., an average light strength of a laser. Other implementations can provide scores, which can be used to determine the base call.

In one embodiment, block 640 can be performed as described in blocks 641 and 642. At block 641, the computer system calculates scores for each of the plurality of bases at a first of the N positions. The calculation uses the basecalling model based on inputs of the intensity values at the N positions. N is an integer equal to or greater than 1. N equals one for a single cycle basecaller, and is greater than one for a multi-cycle basecaller.

A score can correspond to one position or multiple positions. For example, if an intensity value is obtained for a doublet, then a score can be assigned to a particular combination of two bases. In this case, a doublet score still corresponds to a first base being at the first position, but the doublet score also corresponds to a second base being at a second position. In another implementation when an intensity value is obtained for a doublet, an individual score can be obtained for each base of the doublet at a particular one of the two positions.

The scores can be raw scores or processed scores. In one embodiment, a neural network can output raw scores, which can be processed by a post-processing function that modifies the raw scores. For example, the scores can be normalized or be subject to a softmax activation function. This processing can be part of the model, and thus the output scores can be processed scores.

At block 650, the computer system calls the base corresponding to a highest score for the first position when the highest score satisfies one or more criteria. Various criteria may be used. For example, the highest score may be required to be sufficiently larger than a next highest score. As another example, the highest score can be required to be above a threshold. When a score for a doublet is involved, the doublet score with a highest value can be selected, and the base in the first position of the doublet can be called. Base calls can be made for more than one position. For example, base calls can be made for all N positions, or for a subset of the N position. For instance, the scores at the N positions can be used to call bases at M positions (M<N) that are a subset of the M position.

V. Types of Models

In one embodiment, the basecalling model includes a neural network. The neural network can provide flexibility to handle variations across different sequencing runs, e.g., when the training data represents such variations. The neural network can execute efficiently as individual operations are typically multiplications and additions, and other simple functions, such as a linear or sigmoid function. Example sigmoid functions include a hyperbolic tangent sigmoid transfer function $(2/(1+e^{-2x})-1)$ or a log sigmoid transfer function $(1/(1+e^{-x}))$. A basecalling execution speed-up, e.g., due to a simple propagation through a feed-forward neural network, can provide basis for cost reduction. The neural network can be of various types. One type is a multi-layer perceptron (MLP) neural network and another type is a radial basis neural network. Specifically, a neural network may be a multi-layered, non-linear feed forward model.

Figure 7:
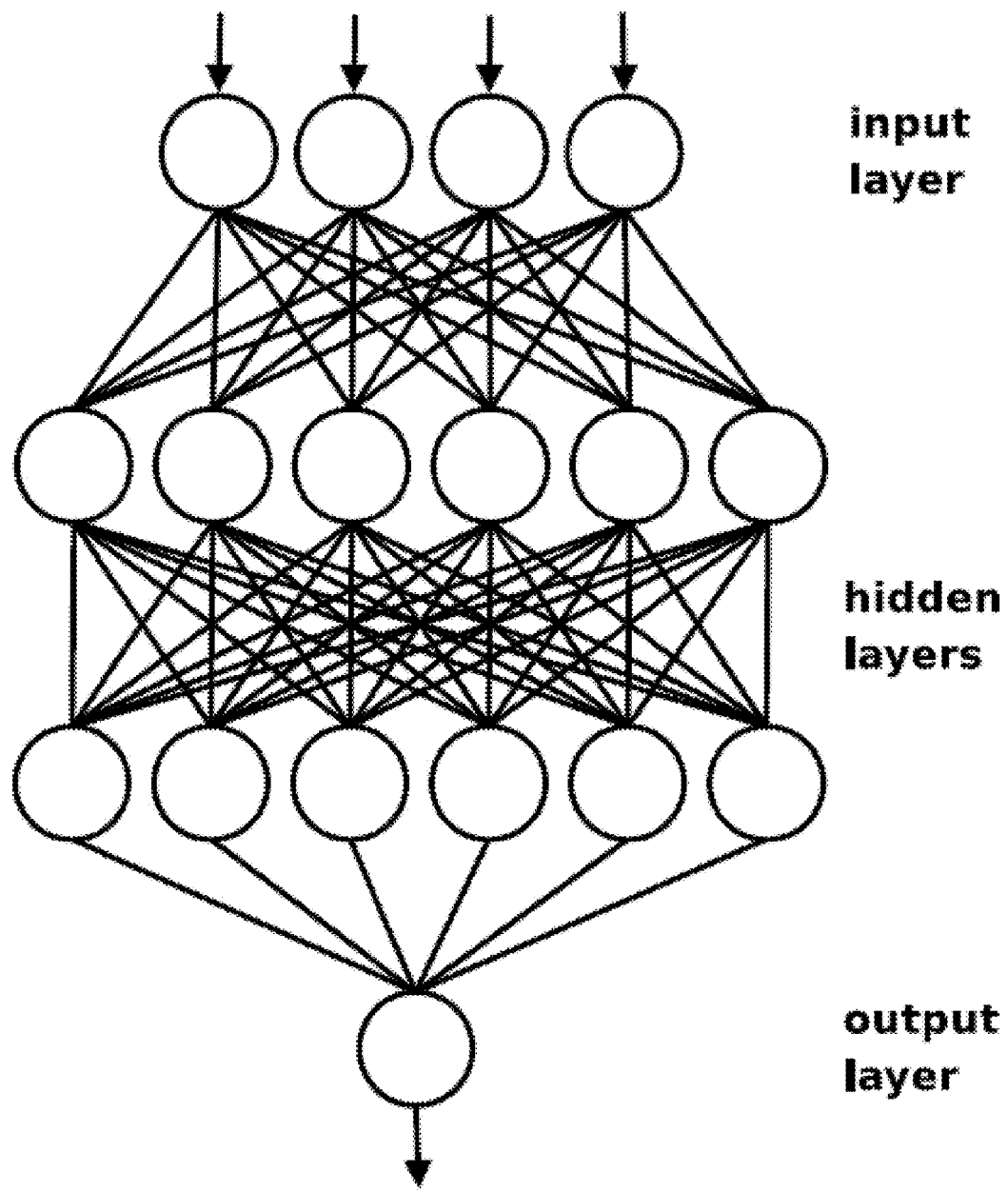
FIG. 7 shows an example neural network according to embodiments of the present invention.

FIG. 7 shows an example neural network according to embodiments of the present invention. Each layer of the neural network is composed of nodes. Each node can receive an input value (e.g., intensity values or outputs from previous layer of neural network), and multiply each of the input values by different weight. The node can then sum the weighted values. The sum can include a bias value that is different for each node. The bias can act as an addition to the sum, where the bias can be added directly or multiplied by the weights and then added. The result can be used directly or input into a function, such as a sigmoidal function. Further layers of the neural network can operate in a similar manner. In various implementations, a sigmoidal function can be implemented to go between −1 and 1, 0 and 2, or 0 and 1. Shifted and scaled versions can also be used. Examples of a sigmoid function are $1/(1+e^{-x})$ or $(1-e^{x})/(1+e^{x})$.

A neural network can provide a predictable number of operations for each base call. The neural network can be implemented in a system that is tailored for the specific operations, or at least take advantage of the predictable number of operations. For example, graphics processors (GPUs) can be used to perform the predictable number multiplications and additions, or other basic functions. Also, given that the number of operations can be predictable, a pipeline can be developed, where later stages can reliably know the speed at which data is provided. This can further reduce computational cost. Since a number of operations can be predictable, a variance in time for providing a final sequence of the organism can be reduced. A neural network can typically provide more predictability than support vector machines, which may be used as the model and whose call time is a function of a variable number of the support vectors (which is mostly variable from one cycle to another). A neural network is also generally less sensitive to errors in the training data relative to support vector machines A. Training (Learning) Algorithm The parameters of the model (e.g., a neural network) can be determined by optimizing a cost function. The cost can be some value associated with getting base calls wrong. Thus, the cost function can include contributions from errors in output sequences (determined as output for current values of the parameters and input of corresponding intensity values) compared to the assumed sequences. Each incorrect base call can be counted the same, or incorrect base calls can contribute differently to the cost function. For example, the correct base call can have a high score that is just a little lower than the highest score of the incorrect base call. Such an incorrect base call my contribute less to the cost function, as an instance where the correct base call is a relatively low score compared to the high score of the incorrect base call. The optimization process can identify the parameters that minimize the errors within the cost function.

The optimization process can use a grid with algorithms to search the parameter space for identifying the parameters that minimize the cost function. In an off-line process, all of the training data (i.e., inputs and outputs) is stored in some type of medium (e.g., mainly in memory) and used during each optimization step. However, when the training data set is large, an off-line process can be prohibitive. In such situations, an online learning process can be used, where the cost is partially minimized as each new training data point (or set of training data points) is received. Thus, the training can be incremental, e.g., a model that is trained based on N patterns can be enhanced with M new patterns (without forgetting the original learning of the original N patterns).

In one implementation, the training can be accelerated by initializing the model parameters, e.g., based on an earlier trained model. This initialization can provide for more reliable and efficient convergence. In some embodiments, the outputs can converge to the actual probability scores for the bases.

B. Combining Multiple Neural Networks

In some embodiments, multiple models (intermediate models) can be combined to make a single model. Different scores can be obtained from each model and then a consensus score can be determined for each base. The different models can be of the same type, but be trained in a different manner (e.g., different training data and different initial values for the parameters of the optimization process, different techniques for determining the assumed sequences, different filtering settings, or other different settings mentioned herein). Accordingly, one model could be more accurate but have a bias due to stringent settings (e.g., threshold for quality of initial base call to include in training data), while the other one may have less bias, thereby overcoming the bias with improved accuracy.

For example, five different scores for A at a particular base position can be obtained from five different models. Since each of the five models would have different errors due to the different training, a combined score can approximate a model that would result from more intensive training, which may be prohibitive from a cost perspective. The combined (composite) score can be computed as an average, such as a weighted average, where different models have different weights, e.g., due to models having higher accuracy. Further, a larger single neural network can get stuck during the training process. Thus, the different models could have different architectures, e.g., number of layers and number of nodes, or be of a different type, such as neural network and support vector machine (SVM).

As another example, each model can be used to determine a respective base call. These respective base calls can be used to determine a consensus base call. For example, the base call that appears the most can be determined as the consensus base call. For instance, if A is called three times, G is called once, and T is called once, then A can be determined as the consensus base call. Thus, a voting of the respective base calls can be used. The votes of each model can be weighted, e.g., due to different assigned accuracies to different models. This voting model can be more appropriate for integration of very different types of models.

As mentioned above, a model can be iteratively improved. Once a first round of training is done, the resulting model can be used as the initial basecaller for a next round of training, which can use new training data. The optimization can also use the parameters of the previous neural network as the starting position for the optimization process. A subsequent training can include new training data by using assembled sequences for determining the assumed sequences, as opposed to just using mapping. The new training data can also be for a current production run, where only some of the data is used to update the existing model. In this manner, the model can address variations that might be specific to the current production run. Different models could also be trained for each field or lane of the current production run.

Various models can also be prepared, and accuracies of the various models can be compared. For example, the number of cycles and a number of neighbors used can be varied, and a model with a low or lowest accuracy can be chosen.

C. Tailoring Models

Different models can also be prepared for different populations of organisms, e.g., based on geographic regions, or different genders. Individuals of the same population often have similar genetic makeup, and thus a model designed specifically for one population may function more accurately for another organism of that population. In such situations, the training data for first model would be gathered from individuals corresponding to that population.

Models can also be tailored to a specific sequencing instrument and/or to a particular part of a sample, e.g., a particular lane of a slide. In this manner, the model does not have to capture the complexity of all machines or all lanes, and thus can potentially be easier to train or provide greater accuracy.

D. Neural Networks for Different Part of Genome

Additionally, different models can be used for different parts of the genome. In this manner, a model can be specifically trained to handle the genetic makeup of the particular region. As each region can have different characteristics, such as GC content, such region-specific models can be more accurate since the amount of variations in inputs is less. Thus, having different models for different regions can make the model more accurate as the complexity that the model has to fit is less, since there is only need to model a relatively small part of the genome.

To use such a region-specific basecaller, a location of a sequence of a nucleic acid would need to be determined. To this end, an initial basecaller can determine the initial calls. Then, the initial sequence can be mapped to a reference to determine which region the sequence is from. The corresponding region-specific model can then be used. The initial basecaller could be a model (e.g., a neural network) that has been modeled to cover all or a large portion of the genome.

VI. Neighbors

As mentioned above, the nucleic acids can be on a substrate in an array, which may be ordered or unordered. On such an array, a nucleic acid would have neighbors. The signals from the neighbors may contribute (e.g., leak over) to the signal detected for the nucleic acid for which a base call is being determined. An example where there is an ordered array (lattice) and a rectangular pattern (e.g., square), nucleic acid would have four near neighbors (top, bottom, left, right) and four next nearest neighbors. The distance from a neighbor can be measured by a number of lattice points that separate the two nucleic acids, e.g., 1 for nearest neighbor, 2 for next-nearest neighbors, etc. In other embodiments, a Euclidean or Manhattan distance (or other distances) for considering two nucleic acids to be neighbors can be measured as an actual distance (e.g., in microns or nanometers), which may be done when a non-ordered array is used. The signal from the nearest neighbors would likely contribute more to the measured intensity values for the nucleic acid being analyzed, than further neighbors. Thus, nearest neighbors can be weighted more than next-nearest neighbors.

As the neighboring signals can impact the measured intensity values for the nucleic acid, the neighboring intensity values can be used as inputs for determining a base call of the nucleic acid. In one embodiment, the neighboring intensity values for the current cycle, or a combination of the neighbors, are used. In another embodiment, neighboring intensity values for previous cycles can also be used. This may be done when output scores are provided for multiple cycles.

VII. Multi-Cycle

As mentioned above, intensity values for multiple cycles can be used to determine the base call for a given cycle. In a production run, the difference between a multi-cycle basecaller and a single-cycle basecaller is the number of inputs. The amount of computational time to determine a base call for either a multi-cycle basecaller or a single-cycle basecaller can be relatively similar, when the model is a neural network on a GPU, since the process is mostly I/O bound.

A multi-cycle basecaller allows for the model to account for biochemical remnants from the previous cycle, or other effects of the other cycles. For example, the nucleic acid at a particular location of an array can be amplified, thereby allowing the signal from the nucleic acid to be more visible. Thus, there are multiple copies of the same nucleic acid being detected. During each cycle, probes are added for hybridization to the nucleic acid. The different copies could undergo different hybridization (e.g., by synthesis or ligation), and thus each copy could emit a different signal.

After each cycle, the probes are to be removed. However, it can happen that not all of the probes are removed from all the copies of the nucleic acid. Thus, a residual signal from the previous base can remain in the intensity value for the current cycle. Further, there could simply be mis-incorporation of the probe onto the nucleic acid for a few of the copies.

The multiple cycles of data can be used in various ways. In one example, previous cycles and the current cycle are used to determine the base for the current cycle. Thus, the input can be of N cycles, where N−1 previous cycles are used. In this example, the output would only be of scores for the current cycle. Such an embodiment can correspond to a moving window with the leading edge of the window corresponding to the current cycle. Cycles after the current cycle could also be used, as remnants of the current cycle can bleed over to future cycles. When multiple cycles are used in this embodiment, a different model can be used for the first cycle, or first couple cycles, until the number of cycles equals the number of previous cycles to be used. The model used for the first couple cycles can be a single-cycle model.

In another example, the input is still of N cycles, but the output can provide scores for each of the N cycles. For example, intensity values for the first five cycles can be used to provide scores of the bases at the first five cycles. In this embodiment, a different basecaller is not needed. If N was 5, and the length of the nucleic acid was 17, then the last set of base calls can be for positions 13-17. Thus, positions 13-15 may be called twice, and the two scores can be combined. In another implementation, the sequencing is performed in multiples of N.

The multiple cycles can correspond to non-sequential positions. For example, one cycle could test position 3, and a next cycle could test position 6 or 8. Or, positions 1, 6, and 12 might be used for input intensity values, and corresponding output intensity values can be obtained. This non-sequential testing can occur when combinatorial probe ligation is used. Thus, the N−1 previous cycles can correspond to various positions of the nucleic acid. Additionally, the previous cycles may not be sequential. For example, the previous fifth and third cycles could be used. Any pattern of the positions and cycles can be used in various multi-cycle schemes. Different models can have different patterns.

VIII. Signal Processing

As mentioned herein, the intensity values used as inputs to the model can be raw intensity values or processed intensity values. As examples, a processing can subtract out background, remove crosstalk effects in a signal of each base caused by signals of the other bases (e.g., by deconvolution), and normalized the intensity values. Such processing can be based on fixed optics of the system, which may not change much or often. But, raw intensity values can still be used, where the model can implicitly address such issues without explicit processing.

For normalization, the intensity values can be scaled such that a uniform range of intensity values is obtained from one sequencing run to another. As an example, the normalization could use the maximum, average, or median intensity value obtained for a given cycle or entire production run. In this manner, the average or maximum intensity for the production run could match the average intensity on which the model was trained. The intensities can be required to be between 0 and 1 to have standardized values from one sample to another. For the removal of crosstalk, the raw intensities can be transformed to purify the channel for each base. The removal of crosstalk can use a deconvolution matrix.

IX. Results

Embodiments can provide various improvements. For example, errors can be reduced. The yield can be increased, e.g., less no-calls. The composition of the calls can more accurately represent the genome being studied. For instance, the resulting confusion matrix can be more representative of the human genome. And, computational costs can be reduced.

A. Reduction in Errors and Increase in Yield

Figure 8:
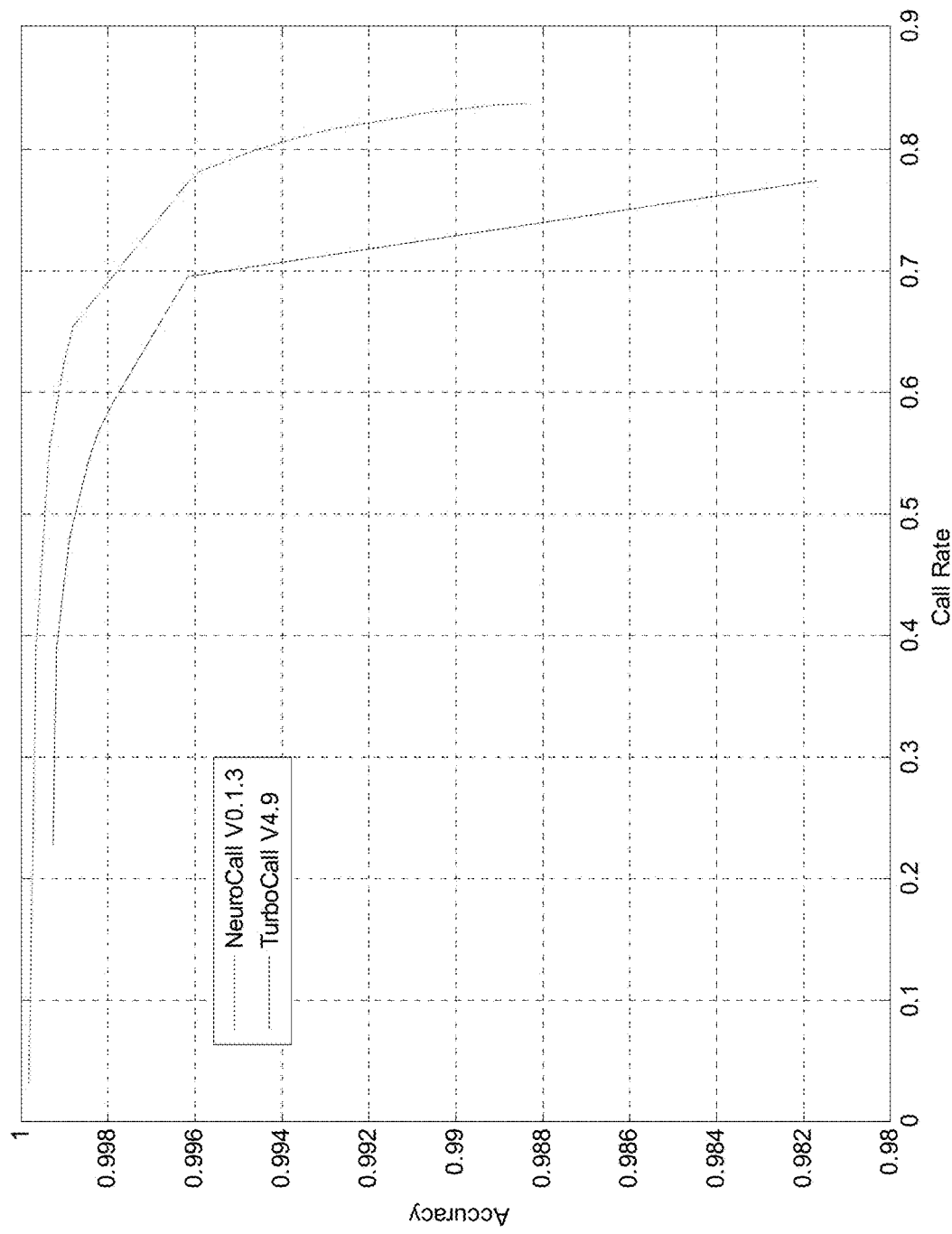
FIG. 8 shows a plot of results comparing the performance of a neural network basecaller (Neurocall) and another basecaller (Turbocall).

FIG. 8 shows a plot of results comparing the performance of a neural network basecaller (Neurocall) and another basecaller (Turbocall). Turbocall only processes the raw signals to reduce crosstalk, e.g., using a crosstalk matrix. The average performance of Neurocall is compared to that of Turbocall for 40 fields (parts of a substrate). As can be seen, the overall quality (accuracy for a given call rate) is twice better, i.e., 100% improvement in the accuracy. Also, the yield (call rate for a given accuracy) is at least 10% improved (from ~70% yield to ~80% yield).

In this example, a multi-layer nonlinear feed-forward neural network was trained on the data from a certain field. Then, the results were loaded for use in each field, and further trained with data from the other fields. The training data comprised approximately 4% of the total data. The trained neural network was then used to call bases on 100% of the data Based on a preliminary simulation, this method of basecalling is capable of providing a higher call rate (additional 10% in yield) and accuracy (100% improvement) as compared to Turbocall, for the same data. Because embodiments can guarantee close to optimal base calling and a most accurate base probability determination for the given data (including noisy and varying), this can allow maximizing basecalling accuracy with inherently noisy two-color-per-cycle encoding scheme that provides two-fold higher sequencing throughput per instrument.

B. Confusion Matrix

Another measure of accuracy is the overall composition of the base calls. The confusion matrix provides information about the probability of a base being called for a different base. For example, if the correct answer is A, but the basecall is C. Such errors would show up in off-diagonal elements. A confusion matrix can also show the content for each base, and thus the GC content is provided in a confusion matrix. The content of each base would correspond to the diagonal elements.

FIG. 9A shows an ideal confusion matrix. The confusion matrix shows expected base calls vs. observed base calls. Ideally, the confusion matrix would have 30% A, 30% T, 20% C, 20% G, which corresponds to the human genome. The off-diagonal elements would be zero. The specific GC percent for a human is around 40.91%, based on Build37 of Human Genome Assembly from NCBI. Embodiments can provide a GC content around 41%, as opposed to other basecallers that provide around 44%. The off-diagonal elements correspond to errors. Ideally, the off-diagonal elements are all roughly the same value, thereby exhibiting uniform noise, and not a bias for one particular error (e.g., errors of A being G).

FIG. 9B shows a confusion matrix according to embodiments of the present invention. As can be seen, the off-diagonal elements are relatively small, with the highest error being 0.18, and thus less than 0.2% for any particular error. Additionally, the variance in the percentage of error from one matrix element to another is not large as it is less than 0.1%. The diagonal elements also mirror the percentages in FIG. 9A.

C. Other Observed Values

Figure 10:
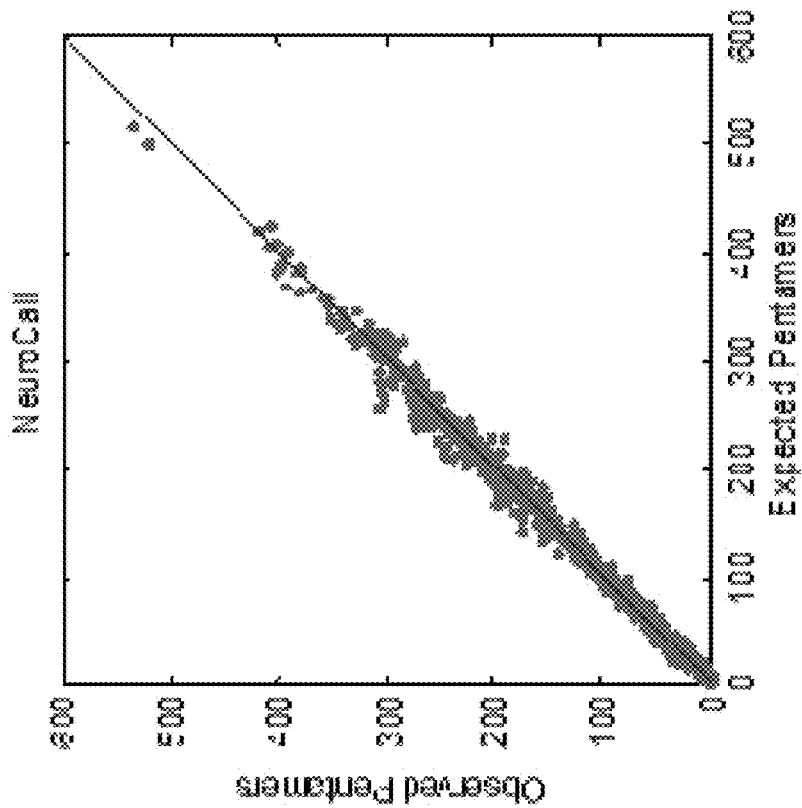
FIG. 10 shows plots illustrating an accuracy of an embodiment of the present invention.
Figure 10:
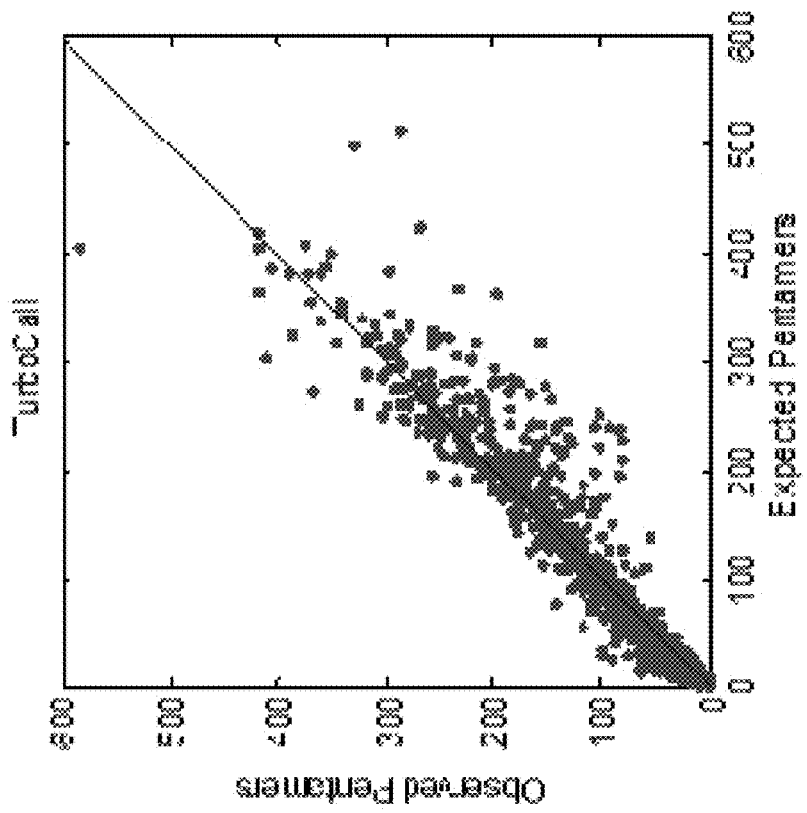

FIG. 10 shows plots illustrating an accuracy of an embodiment of the present invention. Artificial nucleic acids having a known sequence were used. The nucleic acids were of length 5. Different nucleic acids appeared in the set a different number of times. The number of times a particular pentamer appears in the set was noted as an expected value. Thus, each pentamer has an expected frequency in the set. Each data point corresponds to a number of times a particular pentamer was expected and the observer number of called sequences (observed pentamers). Ideally, the data points should lie along a line with a 45 degree slope.

The plots compare the observed vs. expected pentamers using Turbocall (left) and Neurocall (right). A better basecaller should give a scatterplot that is closer to a 45 degree skinny line (i.e., lower dispersion), and it is clear that this is observed in Neurocall relative to Turbocall. Neurocall implements a neural network according to an embodiment of the present invention.

Figure 11:
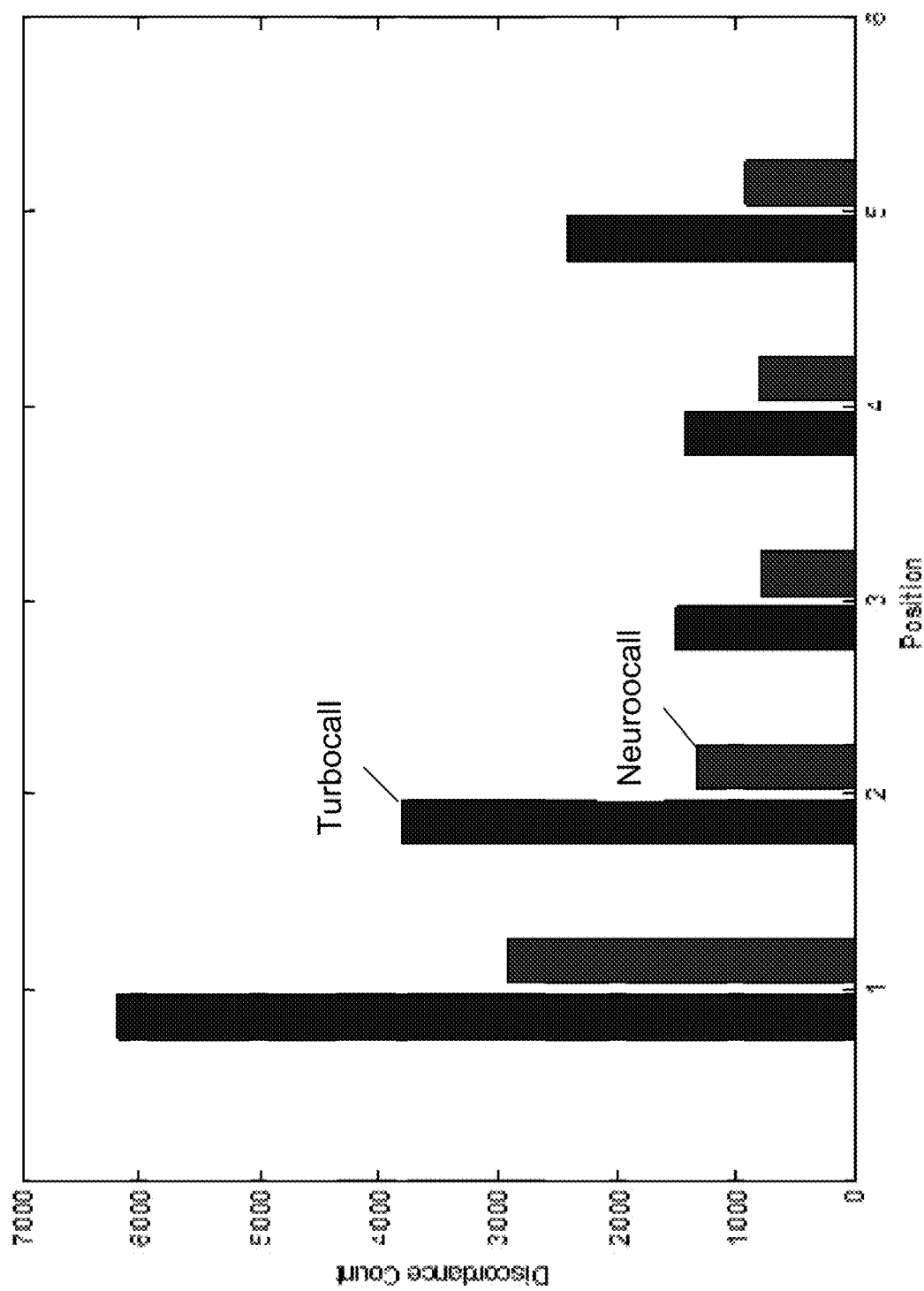
FIG. 11 shows a graph of a comparison of the count of discordant bases for different positions for Neurocall and Turbocall.

FIG. 11 shows a graph of a comparison of the count of discordant bases for different positions. A discordant base is determined via mapping. Thus, a discordant base is one that differs between the reference sequence and the initial sequence that was mapped. The discordance is broken down per position in a pentamer. In this case, the model outputs scores for five positions based on an input of intensity values for the five positions. Pentamers or decamers have been used for training as the set is 10-base Reed-Solomon codes (and not genomic). For any of the 5 positions, the discordance of Neurocall is significantly (2x or better) lower, i.e., better, than that of Turbocall.

For Turbocall, the yield was 76.62%, discordance was 4.85%, and the threshold was 0.04. For Neurocall, the yield was 77.96%, discordance was 2.29%, and the threshold was 0.75.

D. Computational Cost

The computational cost can be measured in terms of speed and storage. Computational speed can relate to an average value and a variation in the speeds to determine each base call. Ideally, an average speed is lower, and the variation in the time to determine a base call is minimized. The variation can have an impact since when you have a production pipeline, there is a need to design for the worst case. This is particularly true when the machine is being designed for a special purpose, or even when more specialized hardware is being used, such as a GPU. The pipeline would need to be designed for the slowest expected operation for the determination of the base call. A larger deviation would provide an even slower expected operation. Thus, a large deviation can cause significant slowdown.

Support vector machines can have a large variation as a number of support vectors can be dynamic for each trained model. When more support vectors are used, more computational time would be used. Thus, the pipeline would be designed such that each operation takes as long as the operation with the most support vectors, even though every operation does not use the maximum number of support vectors.

As mentioned above, neural networks can utilize GPUs. Since a neural network performs repetitive operations of modification, addition, and other basic functions, a neural network can efficiently utilize a GPU. Iterative methods are generally not good for GPUs. The training of a neural network would typically be done with a general-purpose CPU, and then production runs can use GPUs, which can be single precision or double precision.

Also, embodiments can provide short average times. For example, when a neural network is used, the model can only require propagation through several layers of neurons, all of which perform simple mathematical operations, and lend themselves to CPU's built-in parallel processing modes, e.g., Intel's Performance Primitives Library (IPPL). The increase in speed translates directly to a reduction of the system cost, by requiring less CPUs (and consequently less production space and power usage).

X. Computer System

Figure 12:
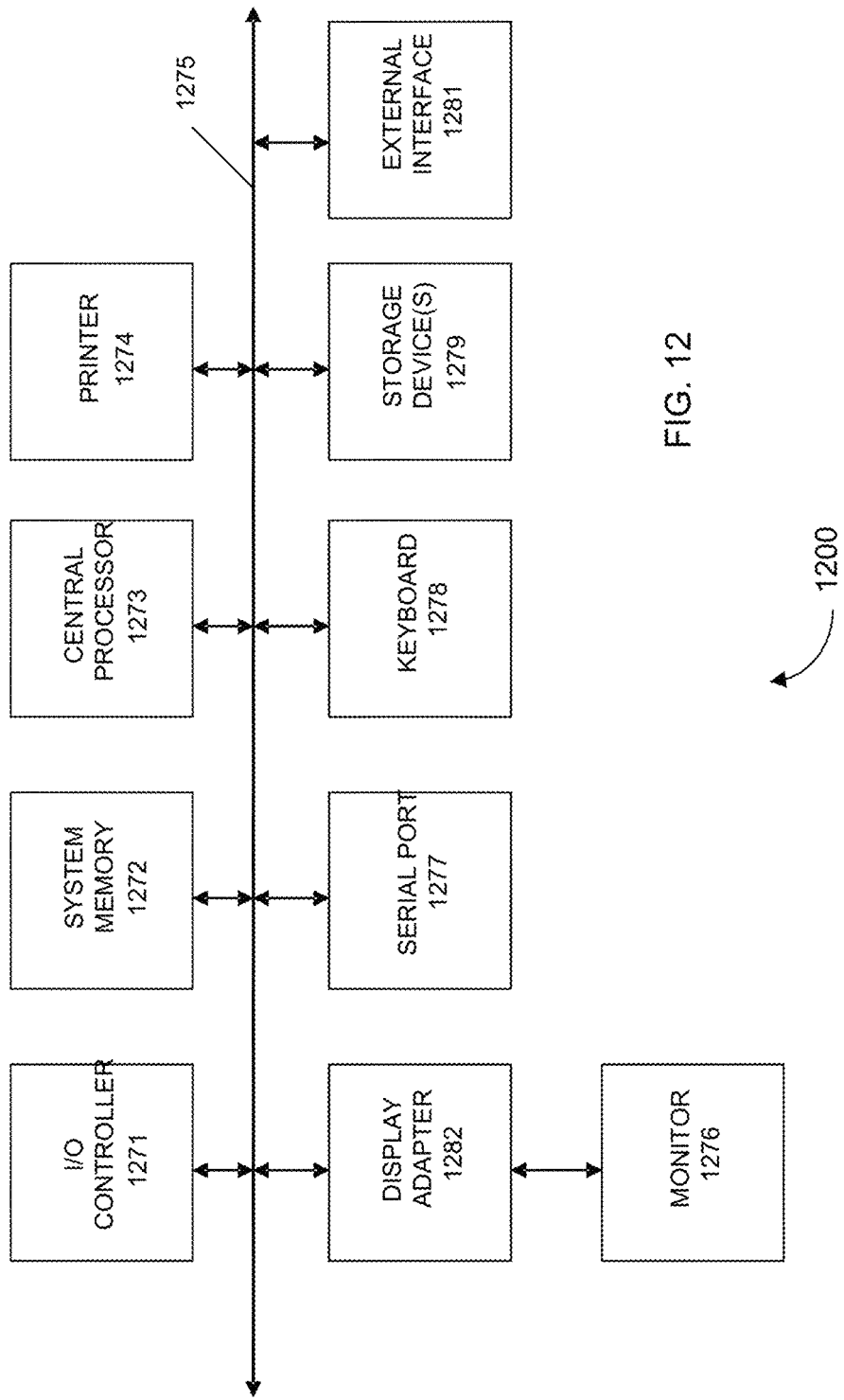
FIG. 12 shows a block diagram of an example computer system 1200 usable with system and methods according to embodiments of the present invention.

Any of the computer systems mentioned herein may utilize any suitable number of subsystems. Examples of such subsystems are shown in FIG. 12 in computer apparatus 1200. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 12 are interconnected via a system bus 1275. Additional subsystems such as a printer 1274, keyboard 1278, storage device(s) 1279, monitor 1276, which is coupled to display adapter 1282, and others are shown. Peripherals and input/output (I/O) devices, which couple to I/O controller 1271, can be connected to the computer system by any number of means known in the art, such as serial port 1277. For example, serial port 1277 or external interface 1281 (e.g. Ethernet, Wi-Fi, etc.) can be used to connect computer system 1200 to a wide area network such as the Internet, a mouse input device, or a scanner. The interconnection via system bus 1275 allows the central processor 1273 to communicate with each subsystem and to control the execution of instructions from system memory 1272 or the storage device(s) 1279 (e.g., a fixed disk, such as a hard drive or optical disk), as well as the exchange of information between subsystems. The system memory 1272 and/or the storage device(s) 1279 may embody a computer readable medium. Any of the data mentioned herein can be output from one component to another component and can be output to the user.

A computer system can include a plurality of the same components or subsystems, e.g., connected together by external interface 1281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C# or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of calling one or more bases for a nucleic acid of an organism, the method comprising:
    receiving, at a computer system, a basecalling model, the basecalling model configured to:
        receive inputs of intensity values for bases at one or more positions on a nucleic acid, and
        output a base call for each of the one or more positions, wherein the basecalling model is trained using a statistically significant number of assumed sequences of training nucleic acids and corresponding intensity values for bases at the positions of the assumed sequences, the corresponding intensity values being obtained from one or more first sequencing processes of training nucleic acids;
    receiving, at the computer system, sequencing data of test nucleic acids from a second sequencing process that is different from any of the one or more first sequencing processes, the sequencing data including intensity values for bases at a plurality of positions of a first test nucleic acid;
    for each of N positions of the first test nucleic acid:
        identifying intensity values corresponding to the position;
    determining, by the computer system, a first base call at a first position of the N positions using the basecalling model based on inputs of the intensity values for the N positions, where N is an integer greater than 1, wherein the basecalling model provides scores for each of a plurality of bases, and wherein determining the first base call includes:
        calculating, by the computer system, scores for each of the plurality of bases at the first position of the N positions using the basecalling model based on inputs of the intensity values for the N positions; and
        calling, by the computer system, the base corresponding to a highest score for the first position when the highest score satisfies one or more criteria; and
    calling a base at M positions based on the scores at the N positions, where M is less than or equal to N and greater than one.

2. The method of claim 1, wherein an intensity value corresponds to a plurality of positions, and each score corresponds to the plurality of positions or to a particular base at one of the plurality of positions.

3. The method of claim 1, wherein the basecalling model includes a neural network.

4. The method of claim 3, wherein the neural network outputs raw scores, and wherein the basecalling model includes a post-processing function that modifies the raw scores.

5. The method of claim 3, wherein the basecalling model includes a plurality of neural networks, the method further comprising:
for each of the plurality of bases:
determining a respective score using each of the plurality of neural networks;
calculating a combined score from the respective scores; and
using the combined score as the score for the base at the first position.

6. The method of claim 1, wherein each intensity value corresponds to one base, and wherein multiple intensity values corresponds to one base.

7. The method of claim 1, further comprising:
performing the second sequencing process on the test nucleic acids.

8. The method of claim 1, wherein the N positions are not sequential.

9. The method of claim 1, wherein the basecalling model includes a plurality of intermediate models, the method further comprising:
for each of the intermediate models:
making a respective base call;
determining a consensus base call from the respective base calls; and
using the consensus base call for the first position.

10. The method of claim 1, wherein the basecalling model is further configured to receive inputs of intensity values for one or more neighboring nucleic acids that neighbor the first test nucleic acid.

11. The method of claim 10, wherein the intensity values for one or more neighboring nucleic acids are for a same cycle as the first position of the first test nucleic acid.

12. The method of claim 10, wherein the one or more neighboring nucleic acids are within a specified distance.

13. The method of claim 12, wherein the first nucleic acid and the one or more neighboring nucleic acids are on an ordered lattice, and wherein the specified distance is a number of lattice points separating the first test nucleic acid and the one or more neighboring nucleic acids.

14. The method of claim 12, wherein the first nucleic acid and the one or more neighboring nucleic acids are not ordered, and wherein the specified distance is a length.

15. A computer product comprising a computer readable medium storing a plurality of instructions for controlling a processor to perform the method of claim 1.

16. The method of claim 1, further comprising creating the basecalling model by:
receiving sequencing data of training nucleic acids from the one or more first sequencing processes, the sequencing data including intensity values for bases at positions of the training nucleic acids, the training nucleic acids being from one or more training samples;
for each of a set of the training nucleic acids:
performing an initial base call at positions of the training nucleic acid to obtain an initial sequence based at least on the intensity values at the positions of the training nucleic acid; and
determining an assumed sequence corresponding to the initial sequence, wherein the assumed sequence is assumed to be a correct sequence for the positions of the training nucleic acid; and
generating the basecalling model using the assumed sequences and the intensity values corresponding to the assumed sequences.

17. A method of calling one or more bases for a nucleic acid of an organism, the method comprising:
receiving, at a computer system, a basecalling model, the basecalling model configured to:
receive inputs of intensity values for bases at one or more positions on a nucleic acid, and
output a base call for each of the one or more positions, wherein the basecalling model is trained using a statistically significant number of assumed sequences of training nucleic acids and corresponding intensity values for bases at the positions of the assumed sequences, the corresponding intensity values being obtained from one or more first sequencing processes of training nucleic acids;
receiving, at the computer system, sequencing data of test nucleic acids from a second sequencing process that is different from any of the one or more first sequencing processes, the sequencing data including intensity values for bases at a plurality of positions of a first test nucleic acid;
for each of N positions of the first test nucleic acid:
identifying intensity values corresponding to the position;
determining, by the computer system, a first base call at a first position of the N positions using the basecalling model based on inputs of the intensity values for the N positions, where N is an integer equal to or greater than 1, wherein the basecalling model provides scores for each of a plurality of bases, and wherein determining the first base call includes:
calculating, by the computer system, scores for each of the plurality of bases at the first position of the N positions using the basecalling model based on inputs of the intensity values for the N positions; and
calling, by the computer system, the base corresponding to a highest score for the first position when the highest score satisfies one or more criteria, and
wherein the one or more criteria include at least one of:
the highest score being greater than a first threshold, and
a difference between the highest score and a next highest score being greater than a second threshold.

18. The method of claim 17, wherein N is greater than 1.

19. The method of claim 17, further comprising:
calculating a confidence score corresponding to the first base call at the first position, wherein the basecalling model includes a support vector machine, and wherein the confidence score is determined based on a separation between a hyperplane and a data point whose multi-dimensional values include:
the intensity values, or
a projection of the intensity values into a multi-dimensional space.

* * * * *